United States Patent
Wu et al.

(10) Patent No.: US 9,994,922 B2
(45) Date of Patent: Jun. 12, 2018

(54) METHODS AND COMPOSITIONS FOR ASSESSING COPY NUMBER OF TARGET POLYNECLEOTIDES

(71) Applicant: NINGBO HEALTH GENE TECHNOLOGY CO., LTD., Ningbo, Zhejiang (CN)

(72) Inventors: Yong Wu, Zhejiang (CN); Tingting Sun, Zhejiang (CN); Linan Wu, Zhejiang (CN); Yingbin Huang, Zhejiang (CN); Jin Yan, Zhejiang (CN); Ding Yu, Zhejiang (CN); Xiangzhen Zan, Zhejiang (CN)

(73) Assignee: Ningbo Health Gene Technologies Co., Ltd. (CN)

( * ) Notice: Subject to any disclaimer, the term of this patent is extended or adjusted under 35 U.S.C. 154(b) by 494 days.

(21) Appl. No.: 14/401,473

(22) PCT Filed: Jun. 21, 2013

(86) PCT No.: PCT/CN2013/077652
§ 371 (c)(1),
(2) Date: Nov. 14, 2014

(87) PCT Pub. No.: WO2013/189306
PCT Pub. Date: Dec. 27, 2013

(65) Prior Publication Data
US 2015/0140547 A1    May 21, 2015

(30) Foreign Application Priority Data
Jun. 21, 2012 (CN) .......................... 2012 1 0206564

(51) Int. Cl.
*C12Q 1/68* (2018.01)
*C12Q 1/70* (2006.01)

(52) U.S. Cl.
CPC ......... *C12Q 1/708* (2013.01); *C12Q 2600/16* (2013.01); *C12Q 2600/166* (2013.01)

(58) Field of Classification Search
None
See application file for complete search history.

(56) References Cited

U.S. PATENT DOCUMENTS

| | | | | |
|---|---|---|---|---|
| 6,066,458 A | * | 5/2000 | Haaland | C12Q 1/6851 435/287.2 |
| 8,980,562 B1 | * | 3/2015 | Manna | C12Q 1/6886 435/6.12 |
| 2003/0068635 A1 | * | 4/2003 | Giesen | C12Q 1/6816 435/6.19 |
| 2005/0112558 A1 | * | 5/2005 | Lo | C12Q 1/701 435/5 |
| 2008/0050746 A1 | * | 2/2008 | McMaster | C12N 1/06 435/6.16 |
| 2013/0116136 A1 | * | 5/2013 | Schmitt | C12Q 1/708 506/9 |

OTHER PUBLICATIONS

Muska et al. Standards and Controls: Concepts for Preparation and Use in Real-time PCR Applications. in: Real-Time PCR in Microbiology: From Diagnosis to Characterization; pp. 101-131. Ian M. Mackay, ed. Caister Academic Press, Norfolk, UK (2007).*
Yang, Mengjie, et al., "Genotyping of 11 human papillomaviruses by multiplex PCT with a GeXP analyzer", Journal of Medical Virology. Apr. 12, 2012, vol. 84, pp. 957-963, (Abstract only).
Zheng, Fanqi, et al., "Establishment and Clinical Evaluation of Multiplex PCR in a Single PCR Tube for Identification of Human Papillomaviruses", Journal of Xianning University (Medical Science). 2009, vol. 23, No. 4, pp. 300-305, (Abstract only).
Peng, Jinyu, et al., "An Advance Standard Curve Method in Fluorescence real-time PCR", Chin J. Lab Med, Jun. 2008, vol. 31, No. 6, pp. 687-689, (Abstract only).

* cited by examiner

*Primary Examiner* — Samuel C Woolwine
(74) *Attorney, Agent, or Firm* — Tarolli, Sundheim, Covell & Tummino LLP

(57) ABSTRACT

The present invention relates to methods and compositions for assessing copy number of a target polynucleotide in a sample, methods and compositions for establishing a standard curve for a target polynucleotide, and the uses of the methods and compositions for detecting a pathogen, e.g., human papillomavirus (HPV).

32 Claims, 2 Drawing Sheets

Figure 1. Electropherogram of HPV 16 positive
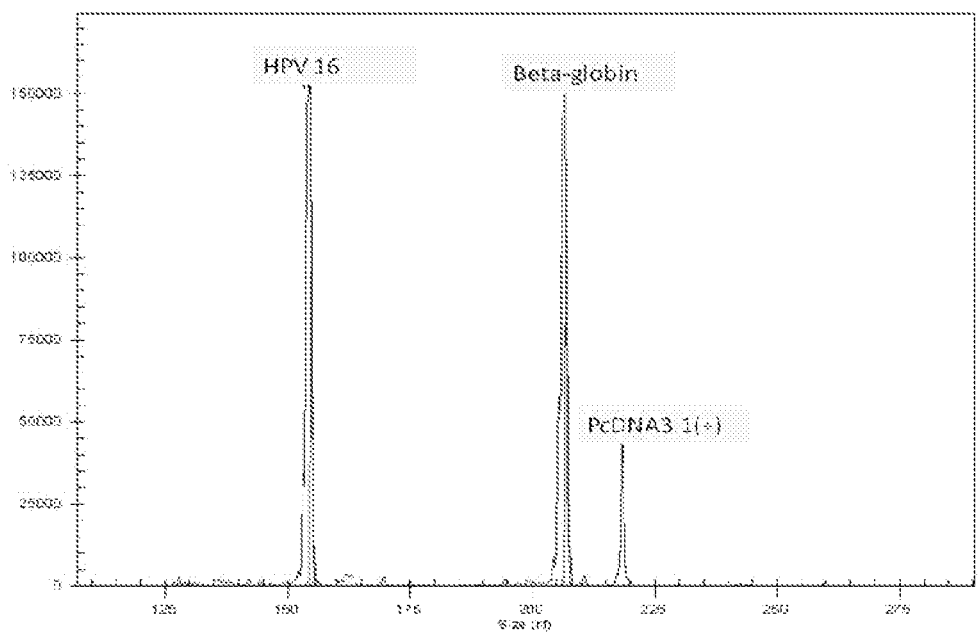
Figure 2. Electropherogram of HPV 53, 52, 81 types positive
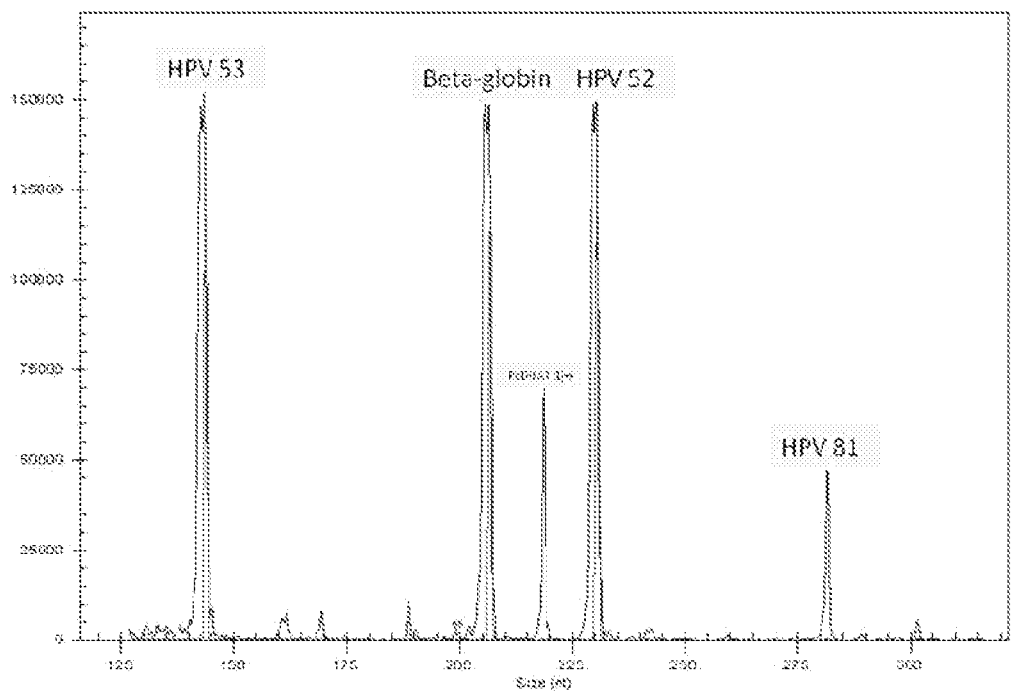

Figure 3.  Electropherogram of HPV negative
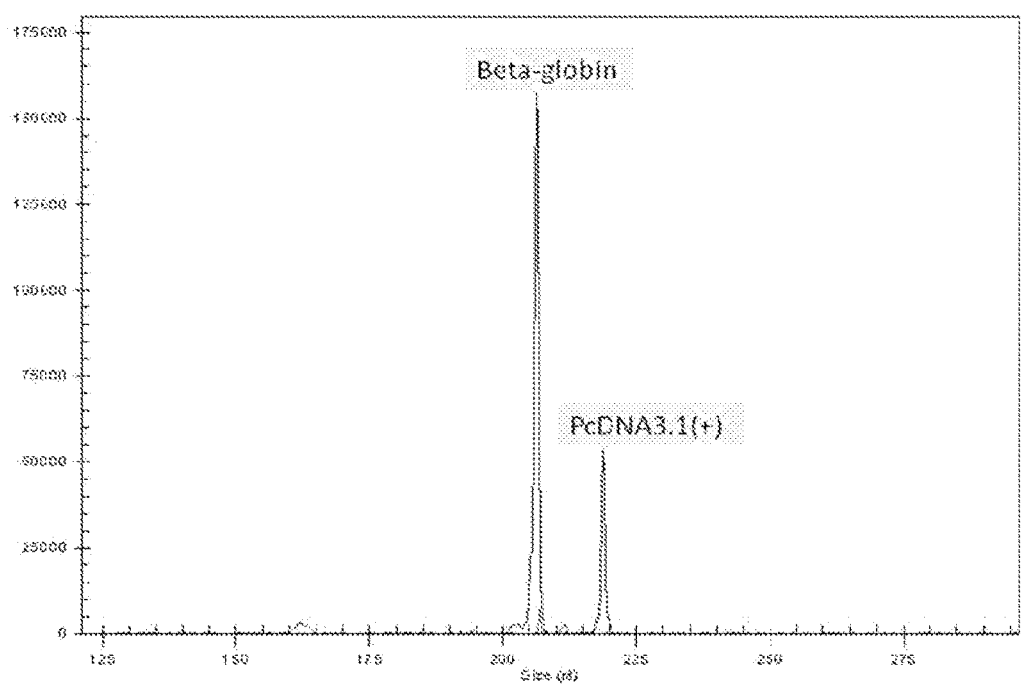

SEQUENCE LISTING

<160> NUMBER OF SEQ ID NOS: 56

<210> SEQ ID NO 1
<211> LENGTH: 18
<212> TYPE: DNA
<213> ORGANISM: Artificial Sequence
<220> FEATURE:
<223> OTHER INFORMATION: Synthetic Universal Primer

<400> SEQUENCE: 1
tcgatgacac tcagacat                                                 18

<210> SEQ ID NO 2
<211> LENGTH: 19
<212> TYPE: DNA
<213> ORGANISM: Artificial Sequence
<220> FEATURE:
<223> OTHER INFORMATION: Synthetic Universal Primer

<400> SEQUENCE: 2
gtacgactca ctataggga                                                19

<210> SEQ ID NO 3
<211> LENGTH: 20
<212> TYPE: DNA
<213> ORGANISM: Artificial Sequence

```
<220> FEATURE:
<223> OTHER INFORMATION: Synthetic primer for HPV type 6

<400> SEQUENCE: 3
acgccgtaaa cgtattccct                                              20

<210> SEQ ID NO 4
<211> LENGTH: 22
<212> TYPE: DNA
<213> ORGANISM: Artificial Sequence
<220> FEATURE:
<223> OTHER INFORMATION: Synthetic Primer for HPV Type 6

<400> SEQUENCE: 4
gatgacccac tgcaagtagt ct                                           22

<210> SEQ ID NO 5
<211> LENGTH: 22
<212> TYPE: DNA
<213> ORGANISM: Artificial Sequence
<220> FEATURE:
<223> OTHER INFORMATION: Synthetic Primer for HPV Type II

<400> SEQUENCE: 5
cagatcatct gtagctagta gt                                           22

<210> SEQ ID NO 6
<211> LENGTH: 20
<212> TYPE: DNA
<213> ORGANISM: Artificial Sequence
<220> FEATURE:
<223> OTHER INFORMATION: Synthetic primer for HPV Type II

<400> SEQUENCE: 6
aaactcctcc acatggcgca                                              20

<210> SEQ ID NO 7
<211> LENGTH: 20
<212> TYPE: DNA
<213> ORGANISM: Artificial Sequence
<220> FEATURE:
<223> OTHER INFORMATION: Synthetic Primer for HPV Type 16

<400> SEQUENCE: 7
ggaggaggat gaaatagatg                                              20

<210> SEQ ID NO 8
<211> LENGTH: 20
<212> TYPE: DNA
<213> ORGANISM: Artificial Sequence
<220> FEATURE:
<223> OTHER INFORMATION: Synthetic Primer for HPV Type 16

<400> SEQUENCE: 8
gctttgtacg cacaaccgaa                                              20

<210> SEQ ID NO 9
<211> LENGTH: 20
<212> TYPE: DNA
<213> ORGANISM: Artificial Sequence
<220> FEATURE:
<223> OTHER INFORMATION: Synthetic primer for HPV Type 18

<400> SEQUENCE: 9
gacgcagaga aacacaagta                                              20
```

```
<210> SEQ ID NO 10
<211> LENGTH: 19
<212> TYPE: DNA
<213> ORGANISM: Artificial Sequence
<220> FEATURE:
<223> OTHER INFORMATION: Synthetic primer for HPV Type 18

<400> SEQUENCE: 10
cgggctggta aatgttgat                                             19

<210> SEQ ID NO 11
<211> LENGTH: 22
<212> TYPE: DNA
<213> ORGANISM: Artificial Sequence
<220> FEATURE:
<223> OTHER INFORMATION: Synthetic primer for HPV Type 26

<400> SEQUENCE: 11
cggtaacagt ggtatttgat tg                                         22

<210> SEQ ID NO 12
<211> LENGTH: 20
<212> TYPE: DNA
<213> ORGANISM: Artificial Sequence
<220> FEATURE:
<223> OTHER INFORMATION: Synthetic primer for HPV Type 26

<400> SEQUENCE: 12
cattgcacac ctgtcccata                                            20

<210> SEQ ID NO 13
<211> LENGTH: 20
<212> TYPE: DNA
<213> ORGANISM: Artificial Sequence
<220> FEATURE:
<223> OTHER INFORMATION: Synthetic primer for HPV Type 31

<400> SEQUENCE: 13
tccttgattg cagtgctggc                                            20

<210> SEQ ID NO 14
<211> LENGTH: 22
<212> TYPE: DNA
<213> ORGANISM: Artificial Sequence
<220> FEATURE:
<223> OTHER INFORMATION: Synthetic primer for HPV 31

<400> SEQUENCE: 14
ctgtaaccga aaacggtgtc at                                         22

<210> SEQ ID NO 15
<211> LENGTH: 23
<212> TYPE: DNA
<213> ORGANISM: Artificial Sequence
<220> FEATURE:
<223> OTHER INFORMATION: Synthetic primerfor HPV Type 33

<400> SEQUENCE: 15
ctatgagcaa ttaagtgaca gct                                        23

<210> SEQ ID NO 16
<211> LENGTH: 22
<212> TYPE: DNA
<213> ORGANISM: Artificial Sequence
<220> FEATURE:
<223> OTHER INFORMATION: Synthetic primer for HPV Type 33
```

```
<400> SEQUENCE: 16
tgtactgttg acacataaac ga                                              22

<210> SEQ ID NO 17
<211> LENGTH: 20
<212> TYPE: DNA
<213> ORGANISM: Artificial Sequence
<220> FEATURE:
<223> OTHER INFORMATION: Synthetic primer for HPV Type 35

<400> SEQUENCE: 17
tgtgtgttcc gctgtgtctt                                                 20

<210> SEQ ID NO 18
<211> LENGTH: 22
<212> TYPE: DNA
<213> ORGANISM: Artificial Sequence
<220> FEATURE:
<223> OTHER INFORMATION: Synthetic primer for HPV Type 35

<400> SEQUENCE: 18
agcgatatgt gtcctctaag gt                                              22

<210> SEQ ID NO 19
<211> LENGTH: 20
<212> TYPE: DNA
<213> ORGANISM: Artificial Sequence
<220> FEATURE:
<223> OTHER INFORMATION: Synthetic primer for HPV Type 39

<400> SEQUENCE: 19
tggccaatcg tgaaggtaca                                                 20

<210> SEQ ID NO 20
<211> LENGTH: 17
<212> TYPE: DNA
<213> ORGANISM: Artificial Sequence
<220> FEATURE:
<223> OTHER INFORMATION: Synthetic primer for HPV Type 39

<400> SEQUENCE: 20
tgtcgccact gctgtct                                                    17

<210> SEQ ID NO 21
<211> LENGTH: 20
<212> TYPE: DNA
<213> ORGANISM: Artificial Sequence
<220> FEATURE:
<223> OTHER INFORMATION: Synthetic primer for HPV Type 42

<400> SEQUENCE: 21
acgaactaag tcctaggctt                                                 20

<210> SEQ ID NO 22
<211> LENGTH: 23
<212> TYPE: DNA
<213> ORGANISM: Artificial Sequence
<220> FEATURE:
<223> OTHER INFORMATION: Synthetic primer for HPV Type 42

<400> SEQUENCE: 22
ctaccaccct tgttgtaggc gta                                             23

<210> SEQ ID NO 23
```

```
<211> LENGTH: 22
<212> TYPE: DNA
<213> ORGANISM: Artificial Sequence
<220> FEATURE:
<223> OTHER INFORMATION: Synthetic primer for HPV Type 43

<400> SEQUENCE: 23
taagtgccac aagccattat ca                                              22

<210> SEQ ID NO 24
<211> LENGTH: 19
<212> TYPE: DNA
<213> ORGANISM: Artificial Sequence
<220> FEATURE:
<223> OTHER INFORMATION: Synthetic primer for HPV Type 43

<400> SEQUENCE: 24
tttccagcaa tgtaagcag                                                  19

<210> SEQ ID NO 25
<211> LENGTH: 20
<212> TYPE: DNA
<213> ORGANISM: Artificial Sequence
<220> FEATURE:
<223> OTHER INFORMATION: Synthetic primer for HPV Type 44

<400> SEQUENCE: 25
atgtgctgcc actacacagt                                                 20

<210> SEQ ID NO 26
<211> LENGTH: 22
<212> TYPE: DNA
<213> ORGANISM: Artificial Sequence
<220> FEATURE:
<223> OTHER INFORMATION: Synthetic primer for HPV Type 44

<400> SEQUENCE: 26
ctctaaggta ccatttgggg gc                                              22

<210> SEQ ID NO 27
<211> LENGTH: 21
<212> TYPE: DNA
<213> ORGANISM: Artificial Sequence
<220> FEATURE:
<223> OTHER INFORMATION: Synthetic primer for HPV Type 45

<400> SEQUENCE: 27
acctaccgtg gactctgttt c                                               21

<210> SEQ ID NO 28
<211> LENGTH: 20
<212> TYPE: DNA
<213> ORGANISM: Artificial Sequence
<220> FEATURE:
<223> OTHER INFORMATION: Synthetic primer for HPV Type 45

<400> SEQUENCE: 28
ctactataca ggcggggacc                                                 20

<210> SEQ ID NO 29
<211> LENGTH: 21
<212> TYPE: DNA
<213> ORGANISM: Artificial Sequence
<220> FEATURE:
<223> OTHER INFORMATION: Synthetic primer for HPV Type 51

<400> SEQUENCE: 29
```
ggctccaccg tgcgcagggt c                                      21

<210> SEQ ID NO 30
<211> LENGTH: 16
<212> TYPE: DNA
<213> ORGANISM: Artificial Sequence
<220> FEATURE:
<223> OTHER INFORMATION: Synthetic primer for HPV Type 51

<400> SEQUENCE: 30
aaaccgcagc agtggc                                            16

<210> SEQ ID NO 31
<211> LENGTH: 20
<212> TYPE: DNA
<213> ORGANISM: Artificial Sequence
<220> FEATURE:
<223> OTHER INFORMATION: Synthetic primer for HPV Type 52

<400> SEQUENCE: 31
gagcaattag gtgacagctc                                        20

<210> SEQ ID NO 32
<211> LENGTH: 22
<212> TYPE: DNA
<213> ORGANISM: Artificial Sequence
<220> FEATURE:
<223> OTHER INFORMATION: Synthetic primer for HPV Type 52

<400> SEQUENCE: 32
aatgtgccca acagcatctg ct                                     22

<210> SEQ ID NO 33
<211> LENGTH: 18
<212> TYPE: DNA
<213> ORGANISM: Artificial Sequence
<220> FEATURE:
<223> OTHER INFORMATION: Synthetic primer for HPV Type 53

<400> SEQUENCE: 33
atggatcgcc agttattt                                          18

<210> SEQ ID NO 34
<211> LENGTH: 22
<212> TYPE: DNA
<213> ORGANISM: Artificial Sequence
<220> FEATURE:
<223> OTHER INFORMATION: Synthetic primer for HPV Type 53

<400> SEQUENCE: 34
acacagccaa gttgcagctc ca                                     22

<210> SEQ ID NO 35
<211> LENGTH: 19
<212> TYPE: DNA
<213> ORGANISM: Artificial Sequence
<220> FEATURE:
<223> OTHER INFORMATION: Synthetic primer for HPV Type 56

<400> SEQUENCE: 35
agtaacgtgc ccactctgc                                         19

<210> SEQ ID NO 36
<211> LENGTH: 20
<212> TYPE: DNA

```
<213> ORGANISM: Artificial Sequence
<220> FEATURE:
<223> OTHER INFORMATION: Synthetic primer for HPV Type 56

<400> SEQUENCE: 36
agctgtctct ctgtctgcct                                              20

<210> SEQ ID NO 37
<211> LENGTH: 22
<212> TYPE: DNA
<213> ORGANISM: Artificial Sequence
<220> FEATURE:
<223> OTHER INFORMATION: Synthetic primer for HPV Type 58

<400> SEQUENCE: 37
cgatggagga aatatcagca cg                                           22

<210> SEQ ID NO 38
<211> LENGTH: 22
<212> TYPE: DNA
<213> ORGANISM: Artificial Sequence
<220> FEATURE:
<223> OTHER INFORMATION: Synthetic primer for HPV Type 58

<400> SEQUENCE: 38
cattatagca cactccatgc gt                                           22

<210> SEQ ID NO 39
<211> LENGTH: 21
<212> TYPE: DNA
<213> ORGANISM: Artificial Sequence
<220> FEATURE:
<223> OTHER INFORMATION: Synthetic primer for HPV Type 59

<400> SEQUENCE: 39
ggacccgagc aagacaccta a                                            21

<210> SEQ ID NO 40
<211> LENGTH: 21
<212> TYPE: DNA
<213> ORGANISM: Artificial Sequence
<220> FEATURE:
<223> OTHER INFORMATION: Synthetic primer for HPV Type 59

<400> SEQUENCE: 40
ctcgtagcac acaaggtcaa c                                            21

<210> SEQ ID NO 41
<211> LENGTH: 20
<212> TYPE: DNA
<213> ORGANISM: Artificial Sequence
<220> FEATURE:
<223> OTHER INFORMATION: Synthetic primer for HPV Type 66

<400> SEQUENCE: 41
ggcgggctat gttcccttag                                              20

<210> SEQ ID NO 42
<211> LENGTH: 20
<212> TYPE: DNA
<213> ORGANISM: Artificial Sequence
<220> FEATURE:
<223> OTHER INFORMATION: Synthetic primer for HPV Type 66

<400> SEQUENCE: 42
gaacaccagc ccctgagtta                                              20
```

-continued

<210> SEQ ID NO 43
<211> LENGTH: 21
<212> TYPE: DNA
<213> ORGANISM: Artificial Sequence
<220> FEATURE:
<223> OTHER INFORMATION: Synthetic primer for HPV Type 68

<400> SEQUENCE: 43
cagtacgttt tagcagagta g                                              21

<210> SEQ ID NO 44
<211> LENGTH: 18
<212> TYPE: DNA
<213> ORGANISM: Artificial Sequence
<220> FEATURE:
<223> OTHER INFORMATION: Synthetic primer for HPV Type 68

<400> SEQUENCE: 44
ccatagggtc agactgct                                                  18

<210> SEQ ID NO 45
<211> LENGTH: 23
<212> TYPE: DNA
<213> ORGANISM: Artificial Sequence
<220> FEATURE:
<223> OTHER INFORMATION: Synthetic primer for HPV Type 73

<400> SEQUENCE: 45
gcagttactc atttgtctgc aat                                            23

<210> SEQ ID NO 46
<211> LENGTH: 24
<212> TYPE: DNA
<213> ORGANISM: Artificial Sequence
<220> FEATURE:
<223> OTHER INFORMATION: Synthetic primer for HPV Type 73

<400> SEQUENCE: 46
gcatttgtgt gatccaaata ggtt                                           24

<210> SEQ ID NO 47
<211> LENGTH: 17
<212> TYPE: DNA
<213> ORGANISM: Artificial Sequence
<220> FEATURE:
<223> OTHER INFORMATION: Synthetic primer for HPV Type 81

<400> SEQUENCE: 47
gggccagcaa accctac                                                   17

<210> SEQ ID NO 48
<211> LENGTH: 20
<212> TYPE: DNA
<213> ORGANISM: Artificial Sequence
<220> FEATURE:
<223> OTHER INFORMATION: Synthetic primer for HPV Type 81

<400> SEQUENCE: 48
gtccgaagca cgaatattgc                                                20

<210> SEQ ID NO 49
<211> LENGTH: 19
<212> TYPE: DNA
<213> ORGANISM: Artificial Sequence
<220> FEATURE:

```
<223> OTHER INFORMATION: Synthetic primer for HPV Type 82

<400> SEQUENCE: 49
ggcaccgggt ctggcactg                                                19

<210> SEQ ID NO 50
<211> LENGTH: 20
<212> TYPE: DNA
<213> ORGANISM: Artificial Sequence
<220> FEATURE:
<223> OTHER INFORMATION: Synthetic primer for HPV Type 82

<400> SEQUENCE: 50
caaagccatc agtaccagta                                               20

<210> SEQ ID NO 51
<211> LENGTH: 22
<212> TYPE: DNA
<213> ORGANISM: Artificial Sequence
<220> FEATURE:
<223> OTHER INFORMATION: Synthetic primer for HPV Type 83

<400> SEQUENCE: 51
gctacggcac tggagccact ca                                            22

<210> SEQ ID NO 52
<211> LENGTH: 18
<212> TYPE: DNA
<213> ORGANISM: Artificial Sequence
<220> FEATURE:
<223> OTHER INFORMATION: Synthetic primer for HPV Type 83

<400> SEQUENCE: 52
taccctacac tggcagca                                                 18

<210> SEQ ID NO 53
<211> LENGTH: 22
<212> TYPE: DNA
<213> ORGANISM: Artificial Sequence
<220> FEATURE:
<223> OTHER INFORMATION: Synthetic primer for the human beta-globin

<400> SEQUENCE: 53
ctcttatctt cctcccacag ct                                            22

<210> SEQ ID NO 54
<211> LENGTH: 22
<212> TYPE: DNA
<213> ORGANISM: Artificial Sequence
<220> FEATURE:
<223> OTHER INFORMATION: Synthetic primer for the human beta-globulin

<400> SEQUENCE: 54
gacttaggga acaaaggaac ct                                            22

<210> SEQ ID NO 55
<211> LENGTH: 20
<212> TYPE: DNA
<213> ORGANISM: Artificial Sequence
<220> FEATURE:
<223> OTHER INFORMATION: Synthetic primer for the PcDNA3.1(+)

<400> SEQUENCE: 55
cagacaatcg gctgctctga                                               20
```

```
<210> SEQ ID NO 56
<211> LENGTH: 19
<212> TYPE: DNA
<213> ORGANISM: Artificial Sequence
<220> FEATURE:
<223> OTHER INFORMATION: Synthetic primer for the PcDNA3.1(+)

<400> SEQUENCE: 56
gcttcagtga caacgtcga                                               19
```

METHODS AND COMPOSITIONS FOR ASSESSING COPY NUMBER OF TARGET POLYNECLEOTIDES

I. CROSS-REFERENCE TO RELATED APPLICATIONS

This application claims the priority benefit of Chinese patent application No. 201210206564.1, filed Jun. 21, 2012, the content of which is incorporated by reference in its entirety.

II. TECHNICAL FIELD

The present invention relates to methods and compositions for assessing copy number of a target polynucleotide in a sample, methods and compositions for establishing a standard curve for a target polynucleotide, and the uses of the methods and compositions for detecting a pathogen, e.g., human papillomavirus (HPV).

III. BACKGROUND OF THE INVENTION

Human papillomavirus (HPV) infects epithelial cells and cause a variety of lesions ranging from common warts/verrucas to cervical neoplasia and cancer. These HPVs fall into "high-risk HPV types" and "low-risk HPV types" depending on the frequency with which they are found in cancers. Cervical cancer is diagnosed in nearly half a million women each year worldwide. It accounts for the second most deaths of all cancers in women. Persistent high-risk HPV infections are now recognized as the cause of essentially all cervical cancers. Therefore, it is very useful to stop the development of high grade cervical neoplasia by early detection and treatment of HPV infections.

Traditionally, genital HPV infection has been detected as abnormal cell changes on a Pap smear, a test used primarily to detect cancer of the cervix or conditions that may lead to cancer. During a Pap smear, the appearance of cervical cells is evaluated under a microscope. Certain changes in the cells may indicate an HPV infection, but there is no clear distinction between high- and low-risk types.

DNA testing for HPV can be used as a follow-up to abnormal changes detected with a Pap smear. The HPV test will continue to be researched and tested as it may be more accurate, alone or combined with Pap testing, when it comes to finding cervical cancer.

Accurate molecular diagnostic techniques that can be used to inform patient management and follow-up after treatment are now available for detection and identification of HPV. Exemplary molecular methods available for HPV detection and genotyping and their possible clinical utility are shown in Table 1 below.

TABLE 1

| HPV DNA test Method Comparison | | |
| --- | --- | --- |
| Method | Advantages | Disadvantages |
| In situ hybridization | Specific | Laborious, time consuming, a big amount DNA needed. |
| Hybrid Capture 2 High-Risk HPV DNA Test | FDA approved, quantitative and detecting High-Risk types. | Low sensitivity compared with PCR, not genotyping. |
| Type-specific PCR Sequencing | specific Good at identifying new HPV types. | Laborious Unsuitable clinically. |
| qPCR | High sensitivity, easy to operate and fast. | Low throughput, 1 to 2 targets in each reaction. |

IV. DISCLOSURE OF THE INVENTION

In one aspect, the present disclosure provides for a method for assessing copy number of a target polynucleotide in a sample, which method comprises: 1) providing a standard curve for a target polynucleotide, wherein said standard curve is established using the following steps: a) providing multiple copy number control compositions, each of said copy number control compositions comprising a set copy number per unit volume of said target polynucleotide, and a first fixed copy number per unit volume of a quantity control polynucleotide, and different copy number control compositions comprising different copy numbers per unit volume of said target polynucleotide; b) conducting a control amplification reaction on said multiple copy number control compositions and said quantity control polynucleotide to amplify said target polynucleotide in said multiple copy number control compositions and said quantity control polynucleotide; c) obtaining a control signal comparison parameter between a signal strength of an amplified target polynucleotide and a signal strength of an amplified quantity control polynucleotide for each of said copy number control compositions; and d) establishing a standard curve for a target polynucleotide, setting forth correlations between said control signal comparison parameter and said set copy number per unit volume of said target polynucleotide in each of said copy number control compositions; 2) conducting a test amplification reaction on a sample containing or suspected of containing a target polynucleotide and a second fixed copy number per unit volume of said quantity control polynucleotide to amplify said target polynucleotide, if present in said sample, and said quantity control polynucleotide, wherein said control and test amplification reactions are the same type of amplification reactions; 3) obtaining a measurement signal comparison parameter between a signal strength of an amplified target polynucleotide and a signal strength of an amplified quantity control polynucleotide from said test amplification reaction; and 4) assessing copy number per unit volume of said target polynucleotide in said sample using said measurement signal comparison parameter and said standard curve. In some embodiments, the present methods are used to detect a pathogen, e.g., human papillomavirus (HPV), in a sample.

In another aspect, the present disclosure provides for a kit or system for assessing copy number of a target polynucleotide in a sample, which kit or system comprises: 1) a standard curve for a target polynucleotide, wherein said standard curve is established using the following steps: a) providing multiple copy number control compositions, each of said copy number control compositions comprising a set copy number per unit volume of said target polynucleotide, and a first fixed copy number per unit volume of a quantity control polynucleotide, and different copy number control compositions comprising different copy numbers per unit volume of said target polynucleotide; b) conducting a control amplification reaction on said multiple copy number control compositions and said quantity control polynucleotide to amplify said target polynucleotide in said multiple copy number control compositions and said quantity control polynucleotide; c) obtaining a control signal comparison parameter between a signal strength of an amplified target polynucleotide and a signal strength of an amplified quantity control polynucleotide for each of said copy number control compositions; and d) establishing a standard curve for a target polynucleotide, setting forth correlations between said control signal comparison parameter and said set copy number per unit volume of said target polynucleotide in each of said copy number control compositions; 2) means for conducting a test amplification reaction on a sample containing or suspected of containing a target polynucleotide and a second fixed copy number per unit volume of said quantity control polynucleotide to amplify said target polynucleotide, if present in said sample, and said quantity control polynucleotide, wherein said control and test amplification reactions are the same type of amplification reactions; and 3) means for obtaining a measurement signal comparison parameter between a signal strength of an amplified target polynucleotide and a signal strength of an amplified quantity control polynucleotide from said test amplification reaction. In some embodiments, the present kits or systems are used to detect a pathogen, e.g., human papillomavirus (HPV), in a sample.

In still another aspect, the present disclosure provides for a method for establishing a standard curve for a target polynucleotide, which method comprises: 1) providing multiple copy number control compositions, each of said copy number control compositions comprising a set copy number per unit volume of said target polynucleotide, and a first fixed copy number per unit volume of a quantity control polynucleotide, and different copy number control compositions comprising different copy numbers per unit volume of said target polynucleotide; 2) conducting a control amplification reaction on said multiple copy number control compositions and said quantity control polynucleotide to amplify said target polynucleotide in said multiple copy number control compositions and said quantity control polynucleotide; 3) obtaining a control signal comparison parameter between a signal strength of an amplified target polynucleotide and a signal strength of an amplified quantity control polynucleotide for each of said copy number control compositions; and 4) establishing a standard curve for a target polynucleotide, setting forth correlations between said control signal comparison parameter and said set copy number per unit volume of said target polynucleotide in each of said copy number control compositions. In some embodiments, the present methods are used for establishing a standard curve for a target polynucleotide, e.g., a HPV target polynucleotide.

In yet another aspect, the present disclosure provides for a kit or system for establishing a standard curve for a target polynucleotide, which kit or system comprises: 1) multiple copy number control compositions, each of said copy number control compositions comprising a set copy number per unit volume of said target polynucleotide, and a first fixed copy number per unit volume of a quantity control polynucleotide, and different copy number control compositions comprising different copy numbers per unit volume of said target polynucleotide; 2) means for conducting a control amplification reaction on said multiple copy number control compositions and said quantity control polynucleotide to amplify said target polynucleotide in said multiple copy number control compositions and said quantity control polynucleotide; and 3) means for obtaining a control signal comparison parameter between a signal strength of an amplified target polynucleotide and a signal strength of an amplified quantity control polynucleotide for each of said copy number control compositions. In some embodiments, the present kits or systems are used for establishing a standard curve for a target polynucleotide, e.g., a HPV target polynucleotide.

In yet another aspect, the present disclosure provides for an isolated polynucleotide which comprises a polynucleotide sequence that exhibits at least 70%, 75%, 80%, 90%, 95%, 99% or 100% identity to any of the HPV, beta-globin and PcDNA3.1(+) polynucleotide sequence set forth in Table 7, wherein said polynucleotide does not comprise a wild-type, full length HPV, beta-globin and PcDNA3.1(+) polynucleotide sequence from which said polynucleotide is derived.

In yet another aspect, the present disclosure provides for a primer composition, which primer composition comprises, consists essentially of or consists of any of the primer pairs set forth in Table 7.

V. BRIEF DESCRIPTION OF THE DRAWINGS

FIG. 1 illustrates electropherogram of an exemplary test on a HPV 16 positive sample.

FIG. 2 illustrates electropherogram of an exemplary test on a HPV 52, 53, and 81 positive sample.

FIG. 3 illustrates electropherogram of an exemplary test on a HPV negative sample.

VI. DETAILED DESCRIPTION OF THE INVENTION

A. Definitions

Unless defined otherwise, all technical and scientific terms used herein have the same meaning as is commonly understood by one of ordinary skill in the art to which this invention belongs. All patents, patent applications (published or unpublished), and other publications referred to herein are incorporated by reference in their entireties. If a definition set forth in this section is contrary to or otherwise inconsistent with a definition set forth in the patents, applications, published applications and other publications that are herein incorporated by reference, the definition set forth in this section prevails over the definition that is incorporated herein by reference.

As used herein, "a" or "an" means "at least one" or "one or more."

As used herein, "mammal" refers to any of the mammalian class of species. Frequently, the term "mammal," as used herein, refers to humans, human subjects or human patients.

As used herein, the term "subject" is not limited to a specific species or sample type. For example, the term "subject" may refer to a patient, and frequently a human patient. However, this term is not limited to humans and thus encompasses a variety of mammalian species.

As used herein the term "sample" refers to anything which may contain an analyte for which an analyte assay is desired. The sample may be a biological sample, such as a biological fluid or a biological tissue. Examples of biological fluids include urine, blood, plasma, serum, saliva, semen, stool, sputum, cerebral spinal fluid, tears, mucus, amniotic fluid or the like. Biological tissues are aggregate of cells, usually of a particular kind together with their intercellular substance that form one of the structural materials of a human, animal, plant, bacterial, fungal or viral structure, including connective, epithelium, muscle and nerve tissues. Examples of biological tissues also include organs, tumors, lymph nodes, arteries and individual cell(s).

The terms "polynucleotide," "oligonucleotide," "nucleic acid" and "nucleic acid molecule" are used interchangeably herein to refer to a polymeric form of nucleotides of any length, e.g., at least 8, 9, 10, 20, 30, 40, 50, 100, 200, 300, 400, 500, 1,000 or more nucleotides, and may comprise ribonucleotides, deoxyribonucleotides, analogs thereof, or mixtures thereof. This term refers only to the primary structure of the molecule. Thus, the term includes triple-, double- and single-stranded deoxyribonucleic acid ("DNA"), as well as triple-, double- and single-stranded ribonucleic acid ("RNA"). It also includes modified, for example by alkylation, and/or by capping, and unmodified forms of the polynucleotide. More particularly, the terms "polynucleotide," "oligonucleotide," "nucleic acid" and "nucleic acid molecule" include polydeoxyribonucleotides (containing 2-deoxy-D-ribose), polyribonucleotides (containing D-ribose), including tRNA, rRNA, hRNA, and mRNA, whether spliced or unspliced, any other type of polynucleotide which is an N- or C-glycoside of a purine or pyrimidine base, and other polymers containing normucleotidic backbones, for example, polyamide (e.g., peptide nucleic acids ("PNAs")) and polymorpholino (commercially available from the Anti-Virals, Inc., Corvallis, Oreg., as Neugene) polymers, and other synthetic sequence-specific nucleic acid polymers providing that the polymers contain nucleobases in a configuration which allows for base pairing and base stacking, such as is found in DNA and RNA. Thus, these terms include, for example, 3'-deoxy-2',5'-DNA, oligodeoxyribonucleotide N3' to P5' phosphoramidates, 2'-O-alkyl-substituted RNA, hybrids between DNA and RNA or between PNAs and DNA or RNA, and also include known types of modifications, for example, labels, alkylation, "caps," substitution of one or more of the nucleotides with an analog, internucleotide modifications such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., aminoalkylphosphoramidates, aminoalkylphosphotriesters), those containing pendant moieties, such as, for example, proteins (including enzymes (e.g. nucleases), toxins, antibodies, signal peptides, poly-L-lysine, etc.), those with intercalators (e.g., acridine, psoralen, etc.), those containing chelates (of, e.g., metals, radioactive metals, boron, oxidative metals, etc.), those containing alkylators, those with modified linkages (e.g., alpha anomeric nucleic acids, etc.), as well as unmodified forms of the polynucleotide or oligonucleotide.

It will be appreciated that, as used herein, the terms "nucleoside" and "nucleotide" will include those moieties which contain not only the known purine and pyrimidine bases, but also other heterocyclic bases which have been modified. Such modifications include methylated purines or pyrimidines, acylated purines or pyrimidines, or other heterocycles. Modified nucleosides or nucleotides can also include modifications on the sugar moiety, e.g., wherein one or more of the hydroxyl groups are replaced with halogen, aliphatic groups, or are functionalized as ethers, amines, or the like. The term "nucleotidic unit" is intended to encompass nucleosides and nucleotides.

"Nucleic acid probe" and "probe" are used interchangeably and refer to a structure comprising a polynucleotide, as defined above, that contains a nucleic acid sequence that can bind to a corresponding target. The polynucleotide regions of probes may be composed of DNA, and/or RNA, and/or synthetic nucleotide analogs.

As used herein, "complementary or matched" means that two nucleic acid sequences have at least 50% sequence identity. Preferably, the two nucleic acid sequences have at least 60%, 70%, 80%, 90%, 95%, 96%, 97%, 98%, 99% or 100% of sequence identity. "Complementary or matched" also means that two nucleic acid sequences can hybridize under low, middle and/or high stringency condition(s).

As used herein, "substantially complementary or substantially matched" means that two nucleic acid sequences have at least 90% sequence identity. Preferably, the two nucleic acid sequences have at least 95%, 96%, 97%, 98%, 99% or 100% of sequence identity. Alternatively, "substantially complementary or substantially matched" means that two nucleic acid sequences can hybridize under high stringency condition(s).

In general, the stability of a hybrid is a function of the ion concentration and temperature. Typically, a hybridization reaction is performed under conditions of lower stringency, followed by washes of varying, but higher, stringency. Moderately stringent hybridization refers to conditions that permit a nucleic acid molecule such as a probe to bind a complementary nucleic acid molecule. The hybridized nucleic acid molecules generally have at least 60% identity, including for example at least any of 70%, 75%, 80%, 85%, 90%, or 95% identity. Moderately stringent conditions are conditions equivalent to hybridization in 50% formamide, 5×Denhardt's solution, 5×SSPE, 0.2% SDS at 42° C., followed by washing in 0.2×SSPE, 0.2% SDS, at 42° C. High stringency conditions can be provided, for example, by hybridization in 50% formamide, 5×Denhardt's solution, 5×SSPE, 0.2% SDS at 42° C., followed by washing in 0.1×SSPE, and 0.1% SDS at 65° C. Low stringency hybridization refers to conditions equivalent to hybridization in 10% formamide, 5×Denhardt's solution, 6×SSPE, 0.2% SDS at 22° C., followed by washing in 1×SSPE, 0.2% SDS, at 37° C. Denhardt's solution contains 1% Ficoll, 1% polyvinylpyrolidone, and 1% bovine serum albumin (BSA). 20×SSPE (sodium chloride, sodium phosphate, ethylene diamide tetraacetic acid (EDTA)) contains 3M sodium chloride, 0.2M sodium phosphate, and 0.025 M EDTA. Other suitable moderate stringency and high stringency hybridization buffers and conditions are well known to those of skill in the art and are described, for example, in Sambrook et al., Molecular Cloning: A Laboratory Manual, 2nd ed., Cold Spring Harbor Press, Plainview, N.Y. (1989); and Ausubel et al., Short Protocols in Molecular Biology, 4th ed., John Wiley & Sons (1999).

Alternatively, substantial complementarity exists when an RNA or DNA strand will hybridize under selective hybridization conditions to its complement. Typically, selective hybridization will occur when there is at least about 65% complementary over a stretch of at least 14 to 25 nucleotides, preferably at least about 75%, more preferably at least about 90% complementary. See Kanehisa (1984) *Nucleic Acids Res.* 12:203-215.

As used herein, "biological sample" refers to any sample obtained from a living or viral source or other source of macromolecules and biomolecules, and includes any cell type or tissue of a subject from which nucleic acid or protein or other macromolecule can be obtained. The biological sample can be a sample obtained directly from a biological source or a sample that is processed. For example, isolated nucleic acids that are amplified constitute a biological sample. Biological samples include, but are not limited to, body fluids, such as blood, plasma, serum, cerebrospinal fluid, synovial fluid, urine and sweat, tissue and organ samples from animals and plants and processed samples derived therefrom. Also included are soil and water samples and other environmental samples, viruses, bacteria, fungi, algae, protozoa and components thereof.

It is understood that aspects and embodiments of the invention described herein include "consisting" and/or "consisting essentially of" aspects and embodiments.

Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Other objects, advantages and features of the present invention will become apparent from the following specification taken in conjunction with the accompanying drawings.

B. Methods and Compositions for Assessing Copy Number of a Target Polynucleotide in a Sample In one aspect, the present disclosure provides a method for assessing copy number of a target polynucleotide in a sample, which method comprises: 1) providing a standard curve for a target polynucleotide, wherein said standard curve is established using the following steps: a) providing multiple copy number control compositions, each of said copy number control compositions comprising a set copy number per unit volume of said target polynucleotide, and a first fixed copy number per unit volume of a quantity control polynucleotide, and different copy number control compositions comprising different copy numbers per unit volume of said target polynucleotide; b) conducting a control amplification reaction on said multiple copy number control compositions and said quantity control polynucleotide to amplify said target polynucleotide in said multiple copy number control compositions and said quantity control polynucleotide; c) obtaining a control signal comparison parameter between a signal strength of an amplified target polynucleotide and a signal strength of an amplified quantity control polynucleotide for each of said copy number control compositions; and d) establishing a standard curve for a target polynucleotide, setting forth correlations between said control signal comparison parameter and said set copy number per unit volume of said target polynucleotide in each of said copy number control compositions; 2) conducting a test amplification reaction on a sample containing or suspected of containing a target polynucleotide and a second fixed copy number per unit volume of said quantity control polynucleotide to amplify said target polynucleotide, if present in said sample, and said quantity control polynucleotide, wherein said control and test amplification reactions are the same type of amplification reactions; 3) obtaining a measurement signal comparison parameter between a signal strength of an amplified target polynucleotide and a signal strength of an amplified quantity control polynucleotide from said test amplification reaction; and 4) assessing copy number per unit volume of said target polynucleotide in said sample using said measurement signal comparison parameter and said standard curve.

Any suitable number of the copy number control compositions can be used in the present methods. In some embodiments, at least 2, 3, 4, 5, 6, 7, 8, 9, 10, 11, 12, 13, 14, 15, 16, 17, 18, 19, 20 or more copy number control compositions are used in the present methods. In other embodiments, the multiple copy number control compositions comprise increasing or decreasing copy numbers per unit volume of the target polynucleotide. In still other embodiments, 16 copy number control compositions are used in the present methods.

The copy number control compositions can comprise any suitable number of the target polynucleotide. In some embodiments, each of the copy number control compositions comprise about 50 copies/µL, 100 copies/µL, 200 copies/µL, 300 copies/µL, 400 copies/µL, 600 copies/µL, 750 copies/µL, 900 copies/µL, 1,200 copies/µL, 1,500 copies/µL, 1,800 copies/µL, 2,500 copies/µL, 3,000 copies/µL, 4,000 copies/µL, 6,000 copies/µL, and 8,000 copies/µL of the target polynucleotide, respectively.

Any suitable level of the quantity control polynucleotide can be used in the present methods. In some embodiments, the first fixed copy number per unit volume comprises about 100 copies/µL, 200 copies/µL, 300 copies/µL, 400 copies/µL, 500 copies/µL, 600 copies/µL, 700 copies/µL, 800 copies/µL, 900 copies/µL, 1,000 copies/µL, 2,000 copies/µL, 3,000 copies/µL, 4,000 copies/µL, 5,000 copies/µL, 6,000 copies/µL, 7,000 copies/µL, 8,000 copies/µL, 9,000 copies/µL, or 10,000 copies/µL of the quantity control polynucleotide.

The present methods can be used to assess copy number of any suitable target polynucleotide in a sample. Similarly, any suitable quantity control polynucleotide can be used in the present methods. In some embodiments, the target polynucleotide and/or the quantity control polynucleotide is a DNA, a RNA or a combination thereof. Preferably, the target polynucleotide and the quantity control polynucleotide are the same or similar type of polynucleotide. For example, both of the target polynucleotide and the quantity control polynucleotide can be DNA or RNA.

Any suitable control amplification reaction and/or the test amplification reaction can be used in the present methods.

Preferably, the control amplification reaction and the test amplification reaction are the same or similar type of polynucleotide amplification reaction. In some embodiments, the control amplification reaction and/or the test amplification reaction is polymerase chain reaction (PCR). Any PCR can be used in the present methods. For example, allele-specific PCR, polymerase cycling assembly (or PCA, also known as assembly PCR), asymmetric PCR, dial-out PCR, helicase-dependent amplification (HDA), hot start PCR, intersequence-specific PCR (ISSR), inverse polymerase chain reaction (Inverse PCR), ligation-mediated PCR, methylation-specific PCR (MSP), miniprimer PCR, multiplex ligation-dependent probe amplification (MLPA), multiplex polymerase chain reaction (multiplex PCR), nested polymerase chain reaction, overlap extension polymerase chain reaction (or OE-PCR), real-time polymerase chain reaction (also called quantitative real time polymerase chain reaction (qPCR) or kinetic polymerase chain reaction), digital polymerase chain reaction (digital PCR, DigitalPCR, dPCR, or dePCR), reverse transcription polymerase chain reaction (RT-PCR), solid phase PCR, thermal asymmetric interlaced PCR (TAIL-PCR), touchdown polymerase chain reaction or touchdown style polymerase chain reaction (step-down PCR), PAN-AC (David, F. and Turlotte, E., (1998). "An Isothermal Amplification Method". C. R. Acad. Sci Paris, Life Science 321 (1): 909-914), universal fast walking, can be used in the present methods.

The signal strength of an amplified target polynucleotide and/or the signal strength of an amplified quantity control polynucleotide in the control amplification reaction can be assessed by any suitable methods. In some embodiments, the signal strength of an amplified target polynucleotide and/or the signal strength of an amplified quantity control polynucleotide in the control amplification reaction is assessed by capillary electrophoresis, gel electrophoresis, or capillary gel electrophoresis. Preferably, the signal strength of an amplified target polynucleotide and the signal strength of an amplified quantity control polynucleotide in the control amplification reaction are assessed by the same or similar type of methods, e.g., capillary electrophoresis, gel electrophoresis, or capillary gel electrophoresis.

The signal strength of an amplified target polynucleotide and/or the signal strength of an amplified quantity control polynucleotide in the test amplification reaction can be assessed by any suitable methods. In some embodiments, the signal strength of an amplified target polynucleotide and/or the signal strength of an amplified quantity control polynucleotide in the test amplification reaction is assessed by capillary electrophoresis, gel electrophoresis, or capillary gel electrophoresis. Preferably, the signal strength of an amplified target polynucleotide and the signal strength of an amplified quantity control polynucleotide in the test amplification reaction are assessed by the same or similar type of methods, e.g., capillary electrophoresis, gel electrophoresis, or capillary gel electrophoresis.

In some embodiments, the signal strength of an amplified target polynucleotide and the signal strength of an amplified quantity control polynucleotide in the control amplification reaction, and the signal strength of an amplified target polynucleotide and the signal strength of an amplified quantity control polynucleotide in the test amplification reaction are assessed by the same or similar type of methods, e.g., capillary electrophoresis, gel electrophoresis, or capillary gel electrophoresis.

The control signal comparison parameter between a signal strength of an amplified target polynucleotide and a signal strength of an amplified quantity control polynucleotide in the control amplification reaction can be in any suitable form. For example, the control signal comparison parameter can be based on the addition, subtraction, multiplication, division, square, square root, or the combination thereof, between a signal strength of an amplified target polynucleotide and a signal strength of an amplified quantity control polynucleotide in the control amplification reaction. In some embodiments, the control signal comparison parameter between a signal strength of an amplified target polynucleotide and a signal strength of an amplified quantity control polynucleotide in the control amplification reaction is a ratio between the peak area of the amplified target polynucleotide and the peak area of the amplified quantity control polynucleotide.

The measurement signal comparison parameter between a signal strength of an amplified target polynucleotide and a signal strength of an amplified quantity control polynucleotide in the test amplification reaction can be in any suitable form. For example, the measurement signal comparison parameter can be based on the addition, subtraction, multiplication, division, square, square root, or the combination thereof, between a signal strength of an amplified target polynucleotide and a signal strength of an amplified quantity control polynucleotide in the test amplification reaction. In some embodiments, the measurement signal comparison parameter between a signal strength of an amplified target polynucleotide and a signal strength of an amplified quantity control polynucleotide in the test amplification reaction is a ratio between the peak area of the amplified target polynucleotide and the peak area of the amplified quantity control polynucleotide.

Preferably, the control signal comparison parameter between a signal strength of an amplified target polynucleotide and a signal strength of an amplified quantity control polynucleotide in the control amplification reaction is the same or similar type of the measurement signal comparison parameter between a signal strength of an amplified target polynucleotide and a signal strength of an amplified quantity control polynucleotide in the test amplification reaction, e.g., a signal comparison parameter can be based on the addition, subtraction, multiplication, division, square, square root, or the combination thereof. In some embodiments, the control signal comparison parameter between a signal strength of an amplified target polynucleotide and a signal strength of an amplified quantity control polynucleotide in the control amplification reaction and the measurement signal comparison parameter between a signal strength of an amplified target polynucleotide and a signal strength of an amplified quantity control polynucleotide in the test amplification reaction are both ratios between the peak area of the amplified target polynucleotide and the peak area of the amplified quantity control polynucleotide.

The standard curve can be in any suitable form. In some embodiments, the standard curve can be in the form of a polynomial curve. The standard curve can further be modified by any suitable curve fitting formulas, techniques and/or processes, e.g., curve fitting involving local southern, interpolation, where an exact fit to the data is required, or smoothing, in which a smooth function is constructed that approximately fits the data, or both.

The first fixed copy number per unit volume of a quantity control polynucleotide used in the control amplification reaction can the same or different from the second fixed copy number per unit volume of the quantity control polynucleotide used in the test amplification reaction. In some embodiments, the first fixed copy number per unit volume of a quantity control polynucleotide used in the control amplification reaction can be substantially identical, e.g., at least 50%, 60%, 70%, 80%, 90%, 95%, or 95% identical, to the second fixed copy number per unit volume of the quantity control polynucleotide used in the test amplification reaction. Preferably, the first fixed copy number per unit volume of a quantity control polynucleotide used in the control amplification reaction can be identical to the second fixed copy number per unit volume of the quantity control polynucleotide used in the test amplification reaction.

In some embodiments, the present method can further comprise using an extraction control polynucleotide in establishing a standard curve in step 1) and assessing copy number of the extraction control polynucleotide in steps 2)-4).

In some embodiments, both the target polynucleotide and the quantity control polynucleotide are DNA molecules, both the control amplification reaction and the test amplification reaction are polymerase chain reactions, and the signal strength of an amplified target polynucleotide and the signal strength of an amplified quantity control polynucleotide in both the control and test amplification reactions are assessed by capillary electrophoresis.

In some embodiments, copy number of a single target polynucleotide in a sample can be assessed by the present methods. In other embodiments, copy numbers of multiple target polynucleotides, e.g., at least 2, 3, 4, 5, 6, 7, 8, 9, 10, 11, 12, 13, 14, 15, 16, 17, 18, 19, 20, 30, 40, 50, 60, 70, 80, 90, 100, 200, 300, 400, 500, 600, 700, 800, 900, 1,000, 10,000 or more target polynucleotides, in a sample can be assessed by the present methods.

In some embodiments, the target polynucleotide that is assessed can be obtained or derived from a biological sample. The biological sample can be any suitable biological sample, e.g., a whole blood, a serum, a plasma, a fresh blood, a blood not containing an anti-coagulate, a urine or a saliva sample.

In some embodiments, the present methods can be used to detect a pathogen in a sample, e.g., by assessing copy number(s) of a single target polynucleotide or multiple target polynucleotides obtained or derived from a pathogen. The present methods can be used to detect any suitable pathogen, e.g., a virus, a bacterium, or a fungus, etc.

In some embodiments, the present methods can be used to detect human papillomavirus (HPV), e.g., by assessing copy number(s) of a single target polynucleotide or multiple target polynucleotides obtained or derived from HPV. For example, copy number(s) of a single target polynucleotide or multiple target polynucleotides obtained or derived from a low-risk HPV type and/or a high-risk HPV type can be assessed by the present methods.

Exemplary low-risk HPV type can be HPV type 6, 11, 42, 43, 44 or 81. In some embodiments, copy numbers of at least 2, 3, 4, 5, and 6 target polynucleotides from low-risk HPV type 6, 11, 42, 43, 44 and 81 can be assessed. Exemplary high-risk HPV type can be HPV type 16, 18, 26, 31, 33, 35, 39, 45, 51, 52, 53, 56, 58, 59, 66, 68, 73, 82 or 83. In some embodiments, copy numbers of at least 2, 3, 4, 5, 6, 7, 8, 9, 10, 11, 12, 13, 14, 15, 16, 17, 18 and 19 target polynucleotides from high-risk HPV type 16, 18, 26, 31, 33, 35, 39, 45, 51, 52, 53, 56, 58, 59, 66, 68, 73, 82 and 83 can be assessed. In other embodiments, copy numbers of target polynucleotides from low-risk HPV type 6, 11, 42, 43, 44 and 81 and copy numbers of target polynucleotides from high-risk HPV type 16, 18, 26, 31, 33, 35, 39, 45, 51, 52, 53, 56, 58, 59, 66, 68, 73, 82 and 83 can be assessed.

In some embodiments, both the target polynucleotide and the quantity control polynucleotide are DNA molecules, both the control amplification reaction and the test amplification reaction are polymerase chain reactions, and the signal strength of an amplified target polynucleotide and the signal strength of an amplified quantity control polynucleotide in both the control and test amplification reactions are assessed by capillary electrophoresis.

HPV types can be identified based on any suitable parameter. For example, HPV types can be identified based on the fragment length showed on the graphs of capillary electrophoresis.

When PCR is used as a control amplification reaction and/or a test amplification reaction, the PCR primer pairs can be targeted on any suitable part of a target polynucleotide. For example, when a method is used to detect HPV, the PCR primer pairs can be targeted on any suitable part of a HPV target polynucleotide, e.g., the oncogenes E1, E6 and/or E7 of each specific HPV type.

Any suitable extraction control polynucleotide and quantity control polynucleotide can be used in the present methods. For example, human β-globin polynucleotide can be used as an extraction control polynucleotide and PcDNA3.1 (+) polynucleotide can be used as a quantity control polynucleotide. In some embodiments, the human β-globin polynucleotide is used to confirm that human and a target polynucleotide, e.g., HPV DNA, are extracted successfully. In other embodiments, the PcDNA3.1(+) polynucleotide is used to confirm that the PCR reaction is conducted successfully.

In some embodiments, a mix of 26 PCR products (25 HPV types target polynucleotides and human β-globin polynucleotide) with known copy number per unit volume are used as a copy number control composition.

In some embodiments, 16 dilutions of the copy number control composition are used to make standard curves for each of the HPV types target polynucleotides and human β-globin polynucleotide.

In some embodiments, the peak area ratio of each of the HPV type target polynucleotides to pcDNA 3.1(+) polynucleotide is used to quantify the copy numbers of the HPV type target polynucleotides.

PCR primers for HPV types target polynucleotides, human β-globin polynucleotide and PcDNA3.1(+) can comprise any suitable sequences. In some embodiments, the sequences of PCR primers for HPV types target polynucleotides, human β-globin polynucleotide and PcDNA3.1(+) are listed in Table 7.

The present methods can be used to assess copy numbers of target polynucleotides of any suitable HPV. In some embodiments, copy numbers of target polynucleotides of human papillomavirus existing in cervical exfoliated cells can be assessed. In other embodiments, the present methods can be used to assess a HPV-associated oropharyngeal cancer, oral cavity cancer, and/or head and neck cancer in a subject from which a sample is obtained or derived.

In some embodiments, copy numbers of at least two target polynucleotides can be assessed. In some embodiments, a comparison parameter between the copy numbers of the at least two target polynucleotides, e.g., a ratio between the copy numbers of the at least two target polynucleotides, can be assessed.

In another aspect, the present disclosure provides for a kit or system for assessing copy number of a target polynucleotide in a sample, which kit or system comprises: 1) a standard curve for a target polynucleotide, wherein said standard curve is established using the following steps: a) providing multiple copy number control compositions, each of said copy number control compositions comprising a set copy number per unit volume of said target polynucleotide, and a first fixed copy number per unit volume of a quantity control polynucleotide, and different copy number control compositions comprising different copy numbers per unit volume of said target polynucleotide; b) conducting a control amplification reaction on said multiple copy number control compositions and said quantity control polynucleotide to amplify said target polynucleotide in said multiple copy number control compositions and said quantity control polynucleotide; c) obtaining a control signal comparison parameter between a signal strength of an amplified target polynucleotide and a signal strength of an amplified quantity control polynucleotide for each of said copy number control compositions; and d) establishing a standard curve for a target polynucleotide, setting forth correlations between said control signal comparison parameter and said set copy number per unit volume of said target polynucleotide in each of said copy number control compositions; 2) means for conducting a test amplification reaction on a sample containing or suspected of containing a target polynucleotide and a second fixed copy number per unit volume of said quantity control polynucleotide to amplify said target polynucleotide, if present in said sample, and said quantity control polynucleotide, wherein said control and test amplification reactions are the same type of amplification reactions; and 3) means for obtaining a measurement signal comparison parameter between a signal strength of an amplified target polynucleotide and a signal strength of an amplified quantity control polynucleotide from said test amplification reaction.

Any suitable means for conducting a test amplification reaction can be used in the present kits or systems. For example, the means for conducting a test amplification reaction can comprise reagents and/or instrument for conducting a polymerase chain reaction (PCR). In some embodiments, reagents for conducting a polymerase chain reaction (PCR) can comprise PCR primers, PCR buffer and a polynucleotide polymerase.

Any suitable means for obtaining a measurement signal can be used in the present kits or systems. For example, the means for obtaining a measurement signal can comprise reagents and/or instrument for conducting capillary electrophoresis, gel electrophoresis, or capillary gel electrophoresis.

The present kits or systems can be used for any suitable purposes. For example, the present kits or systems can be used to detect a pathogen in a sample, e.g., by assessing copy number(s) of a single target polynucleotide or multiple target polynucleotides obtained or derived from a pathogen. The present kits or systems can be used to detect any suitable pathogen, e.g., a virus, a bacterium, or a fungus, etc.

In some embodiments, the present kits or systems can be used to detect human papillomavirus (HPV), e.g., by assessing copy number(s) of a single target polynucleotide or multiple target polynucleotides obtained or derived from HPV. For example, copy number(s) of a single target polynucleotide or multiple target polynucleotides obtained or derived from a low-risk HPV type and/or a high-risk HPV type can be assessed by the present kits or systems.

C. Methods and Compositions for Establishing a Standard Curve for a Target Polynucleotide In still another aspect, the present disclosure provides for a method for establishing a standard curve for a target polynucleotide, which method comprises: 1) providing multiple copy number control compositions, each of said copy number control compositions comprising a set copy number per unit volume of said target polynucleotide, and a first fixed copy number per unit volume of a quantity control polynucleotide, and different copy number control compositions comprising different copy numbers per unit volume of said target polynucleotide; 2) conducting a control amplification reaction on said multiple copy number control compositions and said quantity control polynucleotide to amplify said target polynucleotide in said multiple copy number control compositions and said quantity control polynucleotide; 3) obtaining a control signal comparison parameter between a signal strength of an amplified target polynucleotide and a signal strength of an amplified quantity control polynucleotide for each of said copy number control compositions; and 4) establishing a standard curve for a target polynucleotide, setting forth correlations between said control signal comparison parameter and said set copy number per unit volume of said target polynucleotide in each of said copy number control compositions.

In yet another aspect, the present disclosure provides for a kit or system for establishing a standard curve for a target polynucleotide, which kit or system comprises: 1) multiple copy number control compositions, each of said copy number control compositions comprising a set copy number per unit volume of said target polynucleotide, and a first fixed copy number per unit volume of a quantity control polynucleotide, and different copy number control compositions comprising different copy numbers per unit volume of said target polynucleotide; 2) means for conducting a control amplification reaction on said multiple copy number control compositions and said quantity control polynucleotide to amplify said target polynucleotide in said multiple copy number control compositions and said quantity control polynucleotide; and 3) means for obtaining a control signal comparison parameter between a signal strength of an amplified target polynucleotide and a signal strength of an amplified quantity control polynucleotide for each of said copy number control compositions.

Any suitable number of the copy number control compositions can be used in the present methods, kits and systems. In some embodiments, at least 2, 3, 4, 5, 6, 7, 8, 9, 10, 11, 12, 13, 14, 15, 16, 17, 18, 19, 20 or more copy number control compositions are used in the present methods, kits and systems. In other embodiments, the multiple copy number control compositions comprise increasing or decreasing copy numbers per unit volume of the target polynucleotide. In still other embodiments, 16 copy number control compositions are used in the present methods, kits and systems.

The copy number control compositions can comprise any suitable number of the target polynucleotide. In some embodiments, each of the copy number control compositions comprise about 50 copies/µL, 100 copies/µL, 200 copies/µL, 300 copies/µL, 400 copies/µL, 600 copies/µL, 750 copies/µL, 900 copies/µL, 1,200 copies/µL, 1,500 copies/µL, 1,800 copies/µL, 2,500 copies/µL, 3,000 copies/µL, 4,000 copies/µL, 6,000 copies/µL, and 8,000 copies/pt of the target polynucleotide, respectively.

Any suitable level of the quantity control polynucleotide can be used in the present methods, kits and systems. In some embodiments, the first fixed copy number per unit volume comprises about 100 copies/µL, 200 copies/µL, 300 copies/µL, 400 copies/µL, 500 copies/µL, 600 copies/µL, 700 copies/µL, 800 copies/µL, 900 copies/µL, 1,000 copies/µL, 2,000 copies/µL, 3,000 copies/µL, 4,000 copies/µL, 5,000 copies/µL, 6,000 copies/µL, 7,000 copies/µL, 8,000 copies/μL, 9,000 copies/μL, or 10,000 copies/pt of the quantity control polynucleotide.

The present methods, kits and systems can be used to establishing a standard curve for any suitable target polynucleotide. In some embodiments, the target polynucleotide and/or the quantity control polynucleotide is a DNA, a RNA or a combination thereof. Preferably, the target polynucleotide and the quantity control polynucleotide are the same or similar type of polynucleotide. For example, both of the target polynucleotide and the quantity control polynucleotide can be DNA or RNA.

Any suitable control amplification reaction can be used in the present methods, kits and systems. In some embodiments, the control amplification reaction is polymerase chain reaction (PCR). Any PCR can be used in the present methods. For example, allele-specific PCR, polymerase cycling assembly (or PCA, also known as assembly PCR), asymmetric PCR, dial-out PCR, helicase-dependent amplification (HDA), hot start PCR, intersequence-specific PCR (ISSR), inverse polymerase chain reaction (Inverse PCR), ligation-mediated PCR, methylation-specific PCR (MSP), miniprimer PCR, multiplex ligation-dependent probe amplification (MLPA), multiplex polymerase chain reaction (multiplex PCR), nested polymerase chain reaction, overlap extension polymerase chain reaction (or OE-PCR), real-time polymerase chain reaction (also called quantitative real time polymerase chain reaction (qPCR) or kinetic polymerase chain reaction), digital polymerase chain reaction (digital PCR, DigitalPCR, dPCR, or dePCR), reverse transcription polymerase chain reaction (RT-PCR), solid phase PCR, thermal asymmetric interlaced PCR (TAIL-PCR), touchdown polymerase chain reaction or touchdown style polymerase chain reaction (step-down PCR), PAN-AC (David, F. and Turlotte, E., (1998). "An Isothermal Amplification Method". C. R. Acad. Sci Paris, Life Science 321 (1): 909-914), universal fast walking, can be used in the present methods.

The signal strength of an amplified target polynucleotide and/or the signal strength of an amplified quantity control polynucleotide in the control amplification reaction can be assessed by any suitable methods. In some embodiments, the signal strength of an amplified target polynucleotide and/or the signal strength of an amplified quantity control polynucleotide in the control amplification reaction is assessed by capillary electrophoresis, gel electrophoresis, or capillary gel electrophoresis. Preferably, the signal strength of an amplified target polynucleotide and the signal strength of an amplified quantity control polynucleotide in the control amplification reaction are assessed by the same or similar type of methods, e.g., capillary electrophoresis, gel electrophoresis, or capillary gel electrophoresis.

The control signal comparison parameter between a signal strength of an amplified target polynucleotide and a signal strength of an amplified quantity control polynucleotide in the control amplification reaction can be in any suitable form. For example, the control signal comparison parameter can be based on the addition, subtraction, multiplication, division, square, square root, or the combination thereof, between a signal strength of an amplified target polynucleotide and a signal strength of an amplified quantity control polynucleotide in the control amplification reaction. In some embodiments, the control signal comparison parameter between a signal strength of an amplified target polynucleotide and a signal strength of an amplified quantity control polynucleotide in the control amplification reaction is a ratio between the peak area of the amplified target polynucleotide and the peak area of the amplified quantity control polynucleotide.

The standard curve can be in any suitable form. In some embodiments, the standard curve can be in the form of a polynomial curve. The standard curve can further be modified by any suitable curve fitting formulas, techniques and/or processes, e.g., curve fitting involving local southern, interpolation, where an exact fit to the data is required, or smoothing, in which a smooth function is constructed that approximately fits the data, or both.

In some embodiments, the present methods, kits and systems can further comprise using an extraction control polynucleotide in establishing a standard curve.

In some embodiments, both the target polynucleotide and the quantity control polynucleotide are DNA molecules, the control amplification reaction is polymerase chain reaction, and the signal strength of an amplified target polynucleotide and the signal strength of an amplified quantity control polynucleotide in the control amplification reaction is assessed by capillary electrophoresis.

In some embodiments, the present methods, kits and systems can be used to establish a standard curve for a single target polynucleotide. In other embodiments, the present methods, kits and systems can be used to establish a standard curve for multiple target polynucleotides, e.g., at least 2, 3, 4, 5, 6, 7, 8, 9, 10, 11, 12, 13, 14, 15, 16, 17, 18, 19, 20, 30, 40, 50, 60, 70, 100, 200, 300, 400, 500, 600, 700, 800, 900, 1,000, 10,000 or more target polynucleotides.

In some embodiments, the target polynucleotide can be obtained or derived from a biological sample. The biological sample can be any suitable biological sample, e.g., a whole blood, a serum, a plasma, a fresh blood, a blood not containing an anti-coagulate, a urine or a saliva sample.

In some embodiments, a standard curve established by the present methods, kits and systems can be used in an assay detecting a pathogen in a sample, e.g., by assessing copy number(s) of a single target polynucleotide or multiple target polynucleotides obtained or derived from a pathogen. Exemplary pathogens include a virus, a bacterium, or a fungus, etc.

In some embodiments, a standard curve established by the present methods, kits and systems can be used in an assay for detecting a human papillomavirus (HPV) in a sample, e.g., by assessing copy number(s) of a single target polynucleotide or multiple target polynucleotides obtained or derived from HPV. For example, a standard curve established by the present methods, kits and systems can be used in an assay for assessing copy number(s) of a single target polynucleotide or multiple target polynucleotides obtained or derived from a low-risk HPV type and/or a high-risk HPV type can be assessed by the present methods.

Exemplary low-risk HPV type can be HPV type 6, 11, 42, 43, 44 or 81. In some embodiments, copy numbers of at least 2, 3, 4, 5, and 6 target polynucleotides from low-risk HPV type 6, 11, 42, 43, 44 and 81 can be assessed. Exemplary high-risk HPV type can be HPV type 16, 18, 26, 31, 33, 35, 39, 45, 51, 52, 53, 56, 58, 59, 66, 68, 73, 82 or 83. In some embodiments, copy numbers of at least 2, 3, 4, 5, 6, 7, 8, 9, 10, 11, 12, 13, 14, 15, 16, 17, 18 and 19 target polynucleotides from high-risk HPV type 16, 18, 26, 31, 33, 35, 39, 45, 51, 52, 53, 56, 58, 59, 66, 68, 73, 82 and 83 can be assessed. In other embodiments, copy numbers of target polynucleotides from low-risk HPV type 6, 11, 42, 43, 44 and 81 and copy numbers of target polynucleotides from high-risk HPV type 16, 18, 26, 31, 33, 35, 39, 45, 51, 52, 53, 56, 58, 59, 66, 68, 73, 82 and 83 can be assessed.

HPV types can be identified based on any suitable parameter. For example, HPV types can be identified based on the fragment length showed on the graphs of capillary electrophoresis.

When PCR is used as a control amplification reaction, the PCR primer pairs can be targeted on any suitable part of a target polynucleotide. For example, the PCR primer pairs can be targeted on any suitable part of a HPV target polynucleotide, e.g., the oncogenes E1, E6 and/or E7 of each specific HPV type.

Any suitable extraction control polynucleotide and quantity control polynucleotide can be used in the present methods, kits and systems. For example, human β-globin polynucleotide can be used as an extraction control polynucleotide and PcDNA3.1(+) polynucleotide can be used as a quantity control polynucleotide. In some embodiments, the human β-globin polynucleotide is used to confirm that human and a target polynucleotide, e.g., HPV DNA, are extracted successfully. In other embodiments, the PcDNA3.1(+) polynucleotide is used to confirm that the PCR reaction is conducted successfully.

In some embodiments, a mix of 26 PCR products (25 HPV types target polynucleotides and human β-globin polynucleotide) with known copy number per unit volume are used as a copy number control composition.

In some embodiments, 16 dilutions of the copy number control composition are used to make standard curves for each of the HPV types target polynucleotides and human β-globin polynucleotide.

In some embodiments, the peak area ratio of each of the HPV type target polynucleotides to pcDNA 3.1(+)polynucleotide is used to quantify the copy numbers of the HPV type target polynucleotides.

PCR primers for HPV types target polynucleotides, human β-globin polynucleotide and PcDNA3.1(+) can comprise any suitable sequences. In some embodiments, the sequences of PCR primers for HPV types target polynucleotides, human β-globin polynucleotide and PcDNA3.1(+) are listed in Table 7.

A standard curve(s) established by the present methods, kits and systems can be used in an assay for detecting any suitable HPV, e.g., for assessing copy numbers of target polynucleotides of human papillomavirus existing in cervical exfoliated cells can be assessed. In some embodiments, a standard curve(s) established by the present methods, kits and systems can be used in an assay for assessing a HPV-associated oropharyngeal cancer, oral cavity cancer, and/or head and neck cancer in a subject from which a sample is obtained or derived.

Any suitable means can be used for conducting a control amplification reaction. In some embodiments, the means for conducting a control amplification reaction can comprise reagents and/or instrument for conducting a polymerase chain reaction (PCR). In some embodiments, reagents for conducting a polymerase chain reaction (PCR) can comprise PCR primers, PCR buffer and a polynucleotide polymerase.

Any suitable means can be used for obtaining a control signal. In some embodiments, the means for obtaining a control signal can comprise reagents and/or instrument for conducting capillary electrophoresis.

D. Polynucleotides and Primer Compositions

In yet another aspect, the present disclosure provides for an isolated polynucleotide which comprises a polynucleotide sequence that exhibits at least 70%, 75%, 80%, 90%, 95%, 99% or 100% identity to any of the HPV, beta-globin and PcDNA3.1(+) polynucleotide sequence set forth in Table 7, wherein said polynucleotide does not comprise a wild-type, full length HPV, beta-globin and PcDNA3.1(+) polynucleotide sequence from which said polynucleotide is derived.

In some embodiments, the isolated polynucleotide hybridizes to any of the HPV, beta-globin and PcDNA3.1(+) polynucleotide sequence set forth in Table 7 under moderately or highly stringent conditions.

In some embodiments, the isolated polynucleotide comprises any of the HPV, beta-globin and PcDNA3.1(+) polynucleotide sequence set forth in Table 7.

In some embodiments, the isolated polynucleotide consists essentially of any of the HPV, beta-globin and PcDNA3.1(+) polynucleotide sequence set forth in Table 7.

In some embodiments, the isolated polynucleotide consists of any of the HPV, beta-globin and PcDNA3.1(+) polynucleotide sequence set forth in Table 7.

In some embodiments, the isolated polynucleotide is complementary or substantially complementary to any of the HPV, beta-globin and PcDNA3.1(+) polynucleotide sequence set forth in Table 7.

In some embodiments, the isolated polynucleotide is DNA, RNA or a combination thereof.

In yet another aspect, the present disclosure provides for a primer composition, which primer composition comprises, consists essentially of or consists of any of the primer pairs set forth in Table 7.

In some embodiments, the primer composition comprises, consists essentially of or consists of at least 2, 3, 4, 5, 6, 7, 8, 9, 10, 11, 12, 13, 14, 15, 16, 17, 18, 19, 20, 21, 22, 23, 24 or 25 of the HPV primer pairs set forth in Table 7. In other embodiments, the primer composition further comprises the beta-globin and/or PcDNA3.1(+)primer pair(s) set forth in Table 7.

The polynucleotides or the primers can be made using any suitable methods. For example, the polynucleotides or the primers can be made using chemical synthesis, recombinant production or a combination thereof. See e.g., Molecular Cloning, A Laboratory Manual, Second Edition, Cold Spring Harbor Laboratory Press (1989), Current Protocols in Molecular Biology, John Wiley & Sons (1987-1997) or the like.

E. Exemplary Embodiments

In some embodiments, the present disclosure provides for a multiplex pathogen genotyping and quantitation technique, a HPV kit and its detection procedure. The technique makes it possible to synchronously or simultaneously detect and quantify up to 40 pathogens. The main point of the technique is making a standard curve with known copy number of each pathogen and then quantify the unknown pathogens depends on the standard curve. The HPV kit can synchronously or simultaneously detect and quantify 25 HPV types including 19 high-risk types: 16, 18, 26, 31, 33, 35, 39, 45, 51, 52, 53, 56, 58, 59, 66, 68, 73, 82, 83 and 6 low-risk types: 6, 11, 42, 43, 44, 81. The kit can be useful in early cervical cancer screening and cervical cancer treatment guide. The kit can comprise dNTP and universal primer mix, 10×PCR buffer, HPV primer mix, 25 mM magnesium chloride solution, Taq DNA polymerase, and HPV positive control. The sequence of the primers is provided in the present disclosure. The method can be based on multiplex PCR and capillary electrophoresis (XP-PCR). The test process can include: sample collection; preparation of nucleic acids; PCR amplification with patient nucleic acids as templates; signal separation by capillary electrophoresis (CE); making standard curve; CE data normalization with the internal reaction control; unknown samples quantified by calculation based on the standard curve; data analysis with specific software. Some of the advantages of the present technique and kits are high level of specificity, sensitivity and reliability, quantitation assay of pathogen copy number, high-throughput, low cost, no or low false-negative results.

In some embodiments, the present disclosure provides for a multiplex pathogen genotyping and quantitation technique, a HPV kit and its detection procedure. The technique makes it possible to synchronously detect and quantify up to 40 pathogens. The main point of the technique is making a standard curve with known copy number of each pathogen and then quantify the unknown pathogens depends on the standard curve. The HPV kit can synchronously detect and quantify 25 HPV types including 19 high-risk types: 16, 18, 26, 31, 33, 35, 39, 45, 51, 52, 53, 56, 58, 59, 66, 68, 73, 82, 83 and 6 low-risk types: 6, 11, 42, 43, 44, 81. The kit can comprise dNTP and universal primer mix, 10×PCR buffer, HPV primer mix, 25 mM magnesium chloride solution, Taq DNA polymerase, and HPV positive control. The sequence of the primers is provided in the present disclosure. The method is based on multiplex PCR (XP-PCR) and capillary electrophoresis. Some of the advantages of the present technique and kits are listed below:

1) Multiple HPV types detection: The invention can synchronously detect 25 human papillomavirus types.
2) High-accuracy and high-sensitivity: by means of laser-induced fluorescence-PMT, XP-PCR has a very high signal-to-noise ratio that increases sensitivity and reproducibility across samples for more accurate and informative results.
3) High-specificity: with the proprietary specific primer design and High resolution capillary electrophoretic separation, the XP-PCR technique has a specificity up to >99%.
4) High-throughput: with the capacity to analyze up to 40 target genes per reaction and 192 samples per run, the scalable XP-PCR technique enables the examination of up to 5,760 data points.
5) Internal controls: two internal controls, DNA control and PCR reaction control, enable to avoid false positive and false negative; the internal reaction control is also needed in making standard curve for quantitation of the HPV types.
6) Proprietary sample preparation reagents for easy DNA isolation.
7) Proprietary multiplex PCR reagents for high-performance target amplification.
8) Cost-effective and time-saving: By lowering PCR expenses and improving efficiency, the multiplex power of XP-PCR System enables to analyze up to 40 genes per sample at a dramatically reduced cost per target gene and result with considerable time savings.

The above advantages indicate the present technique and kits may influence HPVs detection in clinical usage significantly compared with the HPV DNA test methods currently used on the market.

In some embodiments, the term "the polymerase chain reaction (PCR)" is a biochemical technology in molecular biology to amplify a single or a few copies of a piece of DNA across several orders of magnitude, generating thousands to millions of copies of a particular DNA sequence.

In some embodiments, "multiplex polymerase chain reaction (Multiplex PCR)" is a modification of polymerase chain reaction in order to rapidly detect deletions or duplications in a large gene. This process amplifies genomic DNA samples using multiple primers and a temperature-mediated DNA polymerase in a thermal cycler. "Quantitative real time polymerase chain reaction (qPCR)" is a laboratory technique based on the polymerase chain reaction, which is used to amplify and simultaneously quantify a targeted DNA molecule.

In some embodiments, "capillary electrophoresis" is designed to separate species based on their size to charge ratio in the interior of a small capillary filled with an electrolyte.

In some embodiments, "deoxyribonucleic acid (DNA)" is a molecule that encodes the genetic instructions used in the development and functioning of all known living organisms and many viruses.

In some embodiments, "human papillomavirus (HPV)" is a virus from the papillomavirus family that is capable of infecting humans.

In some embodiments, "primer" is a strand of nucleic acid that serves as a starting point for DNA synthesis.

In some embodiments, the use of the word "cloning" refers to the fact that the method involves the replication of a single DNA molecule starting from a single living cell to generate a large population of cells containing identical DNA molecules.

In some embodiments, "dNTP and universal primer mix" is a mix of three components in TE buffer. The three components are fluorescence labeled 4-20 μM forward universal primer (sequence: TCGATGACACTCAGACAT, SEQ ID NO:1), 4-20 μM reverse universal primer (sequence: GTACGACTCACTATAGGGA, SEQ ID NO:2) and 3-8 mM dNTP mix.

In some embodiments, "10×PCR Buffer" is comprised of 100 mM Trizma-HCl, pH 8.3 at 25° C., 500 mM KCl and 0.01% (w/v) gelatin.

In some embodiments, "HPV Primer Mix" includes the reverse and forward primers of 25 types of HPV and beta-globin with specific concentration ranged from 20 nM to 300 nM and PcDNA3.1(+) PCR amplification fragments.

1. Primer Design

In some embodiments, all human papillomavirus types referred in this example are targeted on oncogenes E6 and E7—excluding HPV type 39, which is targeted on E1 gene—and specific primer pairs are designed to be used in PCR. The fragment lengths of 25 HPV types and 2 controls are designed to be different. The size difference of two adjacent HPV types is at least 3 nucleotides. Then, after polymerase chain reaction and capillary electrophoresis, HPV type will be identified based on fragment length. See Table 6, 7, 8 for target genes in the present invention, the fragment size and the sequences of the primers.

2. Preparation of HPV Positive Control and HPV Primer Mix

In some embodiments, all the 54 primers including the reverse and forward primers of 25 types of HPV, the reverse and forward primers of a human DNA reference gene beta-globin, and a PCR reaction internal control PcDNA3.1 (+) are confirmed specific via experiments. After PCR amplification, PCR products purification, each DNA fragment is cloned in a commercial vector and then transferred into E. coli for long-term preservation. The E. coli is cultured, and plasmid is extracted with a commercial plasmid extraction kit. Subsequently, through PCR amplification with a common primer pairs which is designed on the both sides of cloning site and gel extraction, DNA fragment containing the specific target sequence is purified. After molecular weight calculation of each fragment and accurate concentration measurement, exact copy number of each fragment solution can be determined. DNA fragments of 25 HPV types and human DNA reference gene beta-globin are mixed and diluted proportionally to make sure the final concentration of each fragment is 100 copies/μL. This mixed fragment solution is HPV Positive Control.

The 54 primers with specific concentration ranged from 20 nM to 300 nM and purified pcDNA3.1(+) PCR amplification fragments with a final concentration 450 copies/μL are mixed together as HPV Primer Mix.

The pcDNA 3.1(+) fragments in the HPV Primer Mix are not added in the HPV Positive Control solution to ensure the copy number of pcDNA 3.1(+) fragments in each PCR reaction is consistent. Nine (9) μL of HPV Positive Control and 2 μL of HPV Primer Mix will be used in PCR reaction; therefore, the final copy number of each HPV type fragments and the fragments of pcDNA 3.1(+) and beta-globin in the 20 μL PCR reaction system are all equally with 900. This copy number 900 equals with virus concentration 5,000 copies/1.5 mL cervical conservation buffer with cervical sample, which is the cut-off point being considered as positive or negative.

3. Making Standard Curve and Sample Quantitation

In some embodiments, first of all, series dilution of 26 DNA fragments mix (fragments of 25 HPV types and human DNA reference gene beta-globin)—50 copies/μL, 100 copies/μL, 200 copies/μL, 300 copies/μL, 400 copies/μL, 600 copies/μL, 750 copies/μL, 900 copies/μL, 1,200 copies/μL, 1,500 copies/μL, 1,800 copies/μL, 2,500 copies/μL, 3,000 copies/μL, 4,000 copies/μL, 6,000 copies/μL, 8,000 copies/μL is done. Secondly, conduct PCR amplification with the dilutions above using HPV kit. Thirdly, compute the peak area ratio of each gene to pcDNA3.1(+) running in the same system. The peak area ratio increases with the increasing concentration of 26 fragments, and then the standard curve of each HPV type is properly made.

When samples are tested, the peak area ratio of each HPV type and beta-globin to pcDNA 3.1(+) fragment in the PCR reaction will be computed specifically for this test. For each gene of the sample, select the four nearest data points in this gene's standard curve points with the above computed peak area ratio, to construct a two polynomial curve. With above peak ratio of each gene and the constructed polynomial curve, we get the copy numbers of the specific HPV types in the testing sample.

4. Methods for Detection and Quantitative Determination of HPV Types

1) Collecting Cervical Samples

Specimens are collected with broom type collection device and then conserved in the cervical conservation buffer.

2) Preparation of Nucleic Acids

In the present embodiment, the platform used in DNA extraction of all cervical samples is Automatic Platform for Magnetic System—Smart LabAssist-16, with TANBead® Viral Auto Plate (96; DNA/RNA virus used), using modified Cat. No./Protocol: 625A46 (Manufacturer: 2006 Taiwan Advanced Nanotech Inc.). Both human and HPV DNA can be extracted from cervical exfoliated cells simultaneously. Other DNA isolation methods are also applicable as long as both human and HPV DNA can be fully extracted from cervical exfoliated cells simultaneously.

3) PCR Amplification with Patient Nucleic Acids or HPV Positive Control as Templates.

TABLE 2

| Twenty (20) μL PCR Reaction System | |
|---|---|
| PCR reagents | Volume/well |
| 10X PCR Buffer | 2 μL |
| 25 mM MgCl$_2$ | 4 μL |
| HPV Primer Mix | 2 μL |
| Taq DNA polymerase | 1 μL |
| dNTP and universal primer mix | 2 μL |
| HPV Positive Control/Sample | 9 μL |

TABLE 3

| PCR reaction condition | | |
|---|---|---|
| Reaction steps | Temperature, time | Cycles |
| 1. Initialization step | 94° C., 60 s | |
| 2. Denaturation step | 94° C., 30 s | 35 cycles |
| 3. Annealing step | 60° C., 30 s | |
| 4. Elongation step | 70° C., 60 s | |
| 5. Final elongation | 70° C., 60 s | |
| 6. Final hold | 4° C., ∞ | |

4) Capillary Electrophoresis Analysis for the PCR Product. Prepare CE loading samples (See Table 4).

TABLE 4

| CE loading sample | |
|---|---|
| CE Component | Quantity per Reaction (μL) |
| Sample loading solution | 38.7 μL |
| DNA size standard 400 | 0.3 μL |
| PCR product | 1 μL |
| Mineral oil | 1 drop |

An exemplary HPV Multiplex Detection Kit" comprises the following components:
HPV Primer mix
dNTP and universal primer mix
10×PCR Buffer
25 mM MgCl$_2$
Taq DNA Polymerase
HPV Positive control.

The present invention is further illustrated by the following exemplary embodiments:

1. A multiplex HPV genotyping kit to detect and quantify 25 HPV types and its detection method.
2. The method and kit of embodiment 1, wherein is based on multiplex PCR and capillary electrophoresis technique.
3. The method and kit of embodiment 1, wherein identify HPV types based on the fragment length showed on the graphs of capillary electrophoresis.
4. The method and kit of embodiment 1, wherein synchronously detect and quantify 25 HPV types, including 6 Low-risk HPV types: 6, 11, 42, 43, 44 and 81, as well as 19 High-risk HPV types: 16, 18, 26, 31, 33, 35, 39, 45, 51, 52, 53, 56, 58, 59, 66, 68, 73, 82 and 83.
5. The method and kit of embodiment 1, wherein all the PCR primer pairs are targeted on the oncogenes E6 and E7 of each specific HPV type.
6. The method and kit of embodiment 1, wherein the sequences of PCR primers for 25 HPV types, beta-globin and PcDNA3.1(+) are listed in Table 7.

7. The method and kit of embodiment 1, wherein there are two controls used: beta-globin and pcDNA3.1(+).
8. The method and of embodiment 7, wherein the human DNA control beta-globin is used to confirm that human and HPV DNA are extracted successfully.
9. The method and of embodiment 7, wherein the PCR reaction control pcDNA 3.1(+) is used to confirm that the PCR reaction was processed successfully.
10. The method and of embodiment 8, wherein if the peak signal of human DNA control beta-globin showed up, it indicates the DNA extraction process is successful; if the peak signal of human DNA control beta-globin is not showed up, it indicates the DNA extraction process is not successful. That will avoid any false positive result.
11. The method and of embodiment 9, wherein if the peak signal of reaction control pcDNA3.1(+) showed up, it will indicate the PCR process is successful; if the peak signal of reaction control pcDNA3.1(+) is not showed up, it will indicate the PCR process is not successful. That will avoid any false negative result.
12. The method and kit of embodiment 1, wherein a mix of 26 PCR products (25 HPV types and beta-globin) with known concentration are used as positive control.
13. The method and kit of embodiment 1, wherein a standard curve is made to quantify the copy numbers of HPV infection.
14. The method and of embodiment 7, wherein the peak area ratio of each HPV type to pcDNA 3.1(+) is used to quantify the copy numbers of HPV infection.
15. The method of embodiments 13-14. wherein 16 dilutions of the 26 PCR products (25 HPV types and beta-globin) with known concentration are used to make standard curve.
16. The method according to embodiments 13-15, wherein the increasing peak area ratio of each HPV type to pcDNA 3.1(+) with the increasing concentration of 26 fragment mix solution gives a formula to calculate the concentration of human papillomavirus in the testing sample.
17. The kit of embodiment 1, wherein the components of the kit are as follows:
 1) HPV Primer mix
 2) Solution X
 3) 10×PCR Buffer
 4) 25 mM MgCl$_2$
 5) Taq DNA Polymerase
 6) HPV Positive Control
18. The kit of embodiment 1, wherein human papillomavirus existed in cervical exfoliated cells can be detected and quantified.
19. The kit of embodiment 1, wherein can detect and quantify human papillomavirus in HPV-associated oropharyngeal cancers, oral cavity cancers, and head and neck cancers.

F. Examples

Example 1

A Patient with HPV Type 16 Infection

After sample collection, preparation of nucleic acids; PCR amplification with patient nucleic acids as templates; signal separation by capillary electrophoresis (CE) and data analysis, electrophoresis graph and analyzed results are shown in FIG. 1.

Example 2

A Patient with HPV Type 53, 52, 81 Infections

After sample collection, preparation of nucleic acids; PCR amplification with patient nucleic acids as templates; signal separation by capillary electrophoresis (CE) and data analysis, electrophoresis graph and analyzed results are shown in FIG. 2.

Example 3

A Patient without HPV Infection

After sample collection, preparation of nucleic acids; PCR amplification with patient nucleic acids as templates; signal separation by capillary electrophoresis (CE) and data analysis, electrophoresis graph and analyzed results are shown in FIG. 3. HPV Negative: DNA control (beta-globin) and PCR reaction control (PcDNA3.1(+)) peaks showed, but no HPV types detected.

Table 6 below illustrates the target genes detected in an exemplary HPV test.

TABLE 6

The target genes detected in this kit

| Risk/Control | HPV types |
| --- | --- |
| High Risk | 16 |
|  | 18 |
|  | 26 |
|  | 31 |
|  | 33 |
|  | 35 |
|  | 39 |
|  | 45 |
|  | 51 |
|  | 52 |
|  | 53 |
|  | 56 |
|  | 58 |
|  | 59 |
|  | 66 |
|  | 68 |
|  | 73 |
|  | 82 |
|  | 83 |
| Low risk | 6 |
|  | 11 |
|  | 42 |
|  | 43 |
|  | 44 |
|  | 81 |
| Human DNA Control | Beta-globin |
| Reaction Control | pcDNA 3.1 (+) |

Table 7 below illustrates sequences of primers of 25 HPV types and 2 controls used in an exemplary HPV test.

TABLE 7

Sequences of primers of 25 HPV types and 2 controls

| HPV Type/Reaction Control | Forward Primer | Reverse Primer |
|---|---|---|
| 6 | SEQ ID NO: 3<br>ACGCCGTAAACGTATTCCCT | SEQ ID NO: 4<br>GATGACCCACTGCAAGTAGTCT |
| 11 | SEQ ID NO: 5<br>CAGATCATCTGTAGCTAGTAGT | SEQ ID NO: 6<br>AAACTCCTCCACATGGCGCA |
| 16 | SEQ ID NO: 7<br>GGAGGAGGATGAAATAGATG | SEQ ID NO: 8<br>GCTTTGTACGCACAACCGAA |
| 18 | SEQ ID NO: 9<br>GACGCAGAGAAACACAAGTA | SEQ ID NO: 10<br>CGGGCTGGTAAATGTTGAT |
| 26 | SEQ ID NO: 11<br>CGGTAACAGTGGTATTTGATTG | SEQ ID NO: 12<br>CATTGCACACCTGTCCCATA |
| 31 | SEQ ID NO: 13<br>TCCTTGATTGCAGTGCTGGC | SEQ ID NO: 14<br>CTGTAACCGAAAACGGTGTCAT |
| 33 | SEQ ID NO: 15<br>CTATGAGCAATTAAGTGACAGCT | SEQ ID NO: 16<br>TGTACTGTTGACACATAAACGA |
| 35 | SEQ ID NO: 17<br>TGTGTGTTCCGCTGTGTCTT | SEQ ID NO: 18<br>AGCGATATGTGTCCTCTAAGGT |
| 39 | SEQ ID NO: 19<br>TGGCCAATCGTGAAGGTACA | SEQ ID NO: 20<br>TGTCGCCACTGCTGTCT |
| 42 | SEQ ID NO: 21<br>ACGAACTAAGTCCTAGGCTT | SEQ ID NO: 22<br>CTACCACCCTTGTTGTAGGCGTA |
| 43 | SEQ ID NO: 23<br>TAAGTGCCACAAGCCATTATCA | SEQ ID NO: 24<br>TTTCCAGCAATGTAAGCAG |
| 44 | SEQ ID NO: 25<br>ATGTGCTGCCACTACACAGT | SEQ ID NO: 26<br>CTCTAAGGTACCATTTGGGGGC |
| 45 | SEQ ID NO: 27<br>ACCTACCGTGGACTCTGTTTC | SEQ ID NO: 28<br>CTACTATACAGGCGGGGACC |
| 51 | SEQ ID NO: 29<br>GGCTCCACCGTGCGCAGGGTC | SEQ ID NO: 30<br>AAACCGCAGCAGTGGC |
| 52 | SEQ ID NO: 31<br>GAGCAATTAGGTGACAGCTC | SEQ ID NO: 31<br>AATGTGCCCAACAGCATCTGCT |
| 53 | SEQ ID NO: 33<br>ATGGATCGCCAGTTATTT | SEQ ID NO: 33<br>ACACAGCCAAGTTGCAGCTCCA |
| 56 | SEQ ID NO: 35<br>AGTAACGTGCCCACTCTGC | SEQ ID NO: 35<br>AGCTGTCTCTCTGTCTGCCT |
| 58 | SEQ ID NO: 37<br>CGATGGAGGAAATATCAGCACG | SEQ ID NO: 37<br>CATTATAGCACACTCCATGCGT |
| 59 | SEQ ID NO: 39<br>GGACCCGAGCAAGACACCTAA | SEQ ID NO: 39<br>CTCGTAGCACACAAGGTCAAC |
| 66 | SEQ ID NO: 41<br>GGCGGGCTATGTTCCCTTAG | SEQ ID NO: 41<br>GAACACCAGCCCCTGAGTTA |
| 68 | SEQ ID NO: 43<br>CAGTACGTTTTAGCAGAGTAG | SEQ ID NO: 43<br>CCATAGGGTCAGACTGCT |
| 73 | SEQ ID NO: 45<br>GCAGTTACTCATTTGTCTGCAAT | SEQ ID NO: 45<br>GCATTTGTGTGATCCAAATAGGTT |
| 81 | SEQ ID NO: 47<br>GGGCCAGCAAACCCTAC | SEQ ID NO: 47<br>GTCCGAAGCACGAATATTGC |
| 82 | SEQ ID NO: 49<br>GGCACCGGGTCTGGCACTG | SEQ ID NO: 50<br>CAAAGCCATCAGTACCAGTA |
| 83 | SEQ ID NO: 51<br>GCTACGGCACTGGAGCCACTCA | SEQ ID NO: 52<br>TACCCTACACTGGCAGCA |

TABLE 7-continued

Sequences of primers of 25 HPV types and 2 controls

| HPV Type/ Reaction Control | Forward Primer | Reverse Primer |
|---|---|---|
| beta-globin | SEQ ID NO: 53 CTCTTATCTTCCTCCCACAGCT | SEQ ID NO: 54 GACTTAGGGAACAAAGGAACCT |
| pcDNA3.1(+) | SEQ ID NO: 55 CAGACAATCGGCTGCTCTGA | SEQ ID NO: 56 GCTTCAGTGACAACGTCGA |

Table 8 below illustrates fragment sizes of 25 HPV types and 2 controls used in an exemplary HPV test.

TABLE 8

Fragment sizes of 25 HPV types and 2 controls

| Type | Size |
|---|---|
| 53 | 143.07 |
| 43 | 149.72 |
| 16 | 154.08 |
| 51 | 158.92 |
| 31 | 164.89 |
| 58 | 169.48 |
| 33 | 183.82 |
| 59 | 188.45 |
| 66 | 194.47 |
| 68 | 200.33 |
| beta-globin | 206.34 |
| 6 | 210.11 |
| pcDNA3.1(+) | 218.57 |
| 18 | 224.23 |
| 52 | 230.14 |
| 83 | 237.83 |
| 26 | 242.83 |
| 82 | 246.19 |
| 44 | 256.34 |
| 73 | 262.5 |
| 35 | 270.03 |
| 56 | 276.64 |
| 81 | 281.72 |
| 45 | 294.13 |
| 42 | 297.91 |
| 11 | 301.73 |
| 39 | 323.14 |

Citation of the above publications or documents is not intended as an admission that any of the foregoing is pertinent prior art, nor does it constitute any admission as to the contents or date of these publications or documents.

The above examples are included for illustrative purposes only and are not intended to limit the scope of the invention. Many variations to those described above are possible. Since modifications and variations to the examples described above will be apparent to those of skill in this art, it is intended that this invention be limited only by the scope of the appended claims.

What is claimed is:

1. A method for simultaneously assessing copy numbers of multiple target polynucleotides in a sample based on multiplex amplification, and signal strength of capillary electrophoresis or gel electrophoresis, which method comprises:
   i) providing standard curves for each of the target polynucleotides, wherein said standard curves are established using the following steps:
      a) providing multiple copy number control compositions, each of said copy number control compositions comprising a set copy number per unit volume of said multiple target polynucleotides, and different copy number control compositions comprising different copy numbers per unit volume of said target polynucleotides;
      b) conducting a control PCR amplification reaction on said multiple copy number control compositions to amplify said target polynucleotides, and within each reaction, a fixed copy number per unit volume of a quantity control polynucleotide is simultaneously amplified;
      c) obtaining control signal comparison parameters between signal strength calculated from peak area of amplified target polynucleotides, and a signal strength, calculated from peak area, of an amplified quantity control polynucleotide in the same reaction for each of said copy number control compositions; and
      d) establishing standard curves for each target polynucleotide, setting forth correlations between said control signal comparison parameters and said set copy number per unit volume of said target polynucleotides in each of said multiple copy number control compositions;
   ii) conducting a test amplification reaction on a sample containing or suspected of containing said target polynucleotides and within the same reaction, a fixed copy number per unit volume of said quantity control polynucleotide is simultaneously amplified;
   iii) obtaining measurement signal comparison parameters between signal strength of amplified target polynucleotides and a signal strength of amplified quantity control polynucleotide from said test amplification reaction; and
   iv) assessing copy number per unit volume of said target polynucleotides in said sample using said measurement signal comparison parameters and said standard curves;
   wherein the signal strength of amplified target polynucleotides and the signal strength of an amplified quantity control polynucleotide in the control amplification reactions and in the test amplification reaction are assessed by capillary electrophoresis or gel electrophoresis.

2. The method of claim 1, wherein 16 copy number control compositions are used.

3. The method of claim 2, wherein each of the copy number control compositions comprise about 50 copies/µL, 100 copies/µL, 200 copies/µL, 300 copies/µL, 400 copies/µL, 600 copies/µL, 750 copies/µL, 900 copies/µL, 1,200 copies/µL, 1,500 copies/µL, 1,800 copies/µL, 2,500 copies/µL, 3,000 copies/µL, 4,000 copies/µL, 6,000 copies/µL, or 8,000 copies/µL of the target polynucleotides, respectively.

4. The method of claim 1, wherein the fixed copy number per unit volume comprises about 100 copies/µL, 200 copies/µL, 300 copies/µL, 400 copies/µL, 500 copies/µL, 600 copies/µL, 700 copies/µL, 800 copies/µL, 900 copies/µL, 1,000 copies/µL, 2,000 copies/µL, 3,000 copies/µL, 4,000 copies/µL, 5,000 copies/µL, 6,000 copies/µL, 7,000 copies/µL, 8,000 copies/µL, 9,000 copies/µL, or 10,000 copies/µL of the quantity control polynucleotide.

5. The method of claim 1, wherein the target polynucleotide and/or the quantity control polynucleotide is DNA or RNA.

6. The method of claim 1, wherein the control amplification reaction and/or the test amplification reaction is polymerase chain reaction (PCR).

7. The method of claim 1, wherein the standard curves are in the form of polynomial curves.

8. The method of claim 1, which further comprises using an extraction control polynucleotide in establishing standard curves in step i) and assessing copy number of the extraction control polynucleotide in steps ii)-iv).

9. The method of claim 1, wherein both the target polynucleotides and the quantity control polynucleotide are DNA molecules, both the target polynucleotides and the quantity control polynucleotide are amplified in the same polymerase chain reaction, and the signal strength of amplified target polynucleotides and the signal strength of an amplified quantity control polynucleotide are assessed by capillary electrophoresis.

10. The method of claim 1, wherein copy number of a single target polynucleotide in a sample is assessed.

11. The method claim 1, wherein copy numbers of multiple target polynucleotides in a sample are simultaneously assessed.

12. The method of claim 1, wherein the target polynucleotide is obtained or derived from a biological sample.

13. The method of claim 12, wherein the biological sample is selected from the group consisting of a whole blood, a serum, a plasma, a fresh blood, a blood not containing an anti-coagulate, a urine and a saliva sample.

14. The method of claim 1, which is used to detect a pathogen in a sample.

15. The method of claim 14, wherein the pathogen is human papillomavirus (HPV).

16. The method of claim 15, wherein copy number of a target polynucleotide from a low-risk HPV type and copy number of a target polynucleotide from high-risk HPV type are assessed.

17. The method of claim 16, wherein the low-risk HPV type is selected from the group consisting of HPV type 6, 11, 42, 43, 44 and 81.

18. The method of claim 16, wherein the high-risk HPV type is selected from the group consisting of HPV type 16, 18, 26, 31, 33, 35, 39, 45, 51, 52, 53, 56, 58, 59, 66, 68, 73, 82 and 83.

19. The method of claim 16, wherein copy numbers of at least 2 target polynucleotides from low-risk HPV type 6, 11, 42, 43, 44 and 81 are assessed.

20. The method of claim 16, wherein copy numbers of at least 2 target polynucleotides from high-risk HPV type 16, 18, 26, 31, 33, 35, 39, 45, 51, 52, 53, 56, 58, 59, 66, 68, 73, 82 and 83 are assessed.

21. The method of claim 15, wherein copy numbers of target polynucleotides of human papillomavirus existing in cervical exfoliated cells are assessed.

22. The method of claim 15, which is used to assess a HPV-associated oropharyngeal cancer, oral cavity cancer, and/or head and neck cancer in a subject from which a sample is obtained or derived.

23. The method of claim 1, wherein copy numbers of target polynucleotides from low-risk HPV type 6, 11, 42, 43, 44 and 81 and copy numbers of target polynucleotides from high-risk HPV type 16, 18, 26, 31, 33, 35, 39, 45, 51, 52, 53, 56, 58, 59, 66, 68, 73, 82 and 83 are assessed.

24. The method of claim 23, wherein HPV types are identified based on amplicon length as determined by capillary electrophoresis.

25. The method of claim 23, wherein the PCR primer pairs are targeted on oncogenes E1, E6 and/or E7 of each specific HPV type.

26. The method of claim 23, wherein the peak area ratio of each of the HPV type target polynucleotides to the quantity control polynucleotide, wherein PcDNA3.1(+) polynucleotide is used as the quantity control polynucleotide, is used to quantify the copy numbers of the HPV type target polynucleotides.

27. The method of claim 1, which further uses human beta-globin polynucleotide as an extraction control polynucleotide and PcDNA3.1(+) polynucleotide as a quantity control polynucleotide.

28. The method of claim 27, wherein the human beta-globin polynucleotide is used to confirm that human and HPV DNA are extracted successfully.

29. The method of claim 27, wherein the PcDNA3.1(+) polynucleotide is used to confirm that the PCR reaction is conducted successfully.

30. The method of claim 1, wherein each copy control number composition comprises a mixture of 26 PCR products with known copy number per unit volume.

31. The method of claim 30, wherein 16 dilutions of the copy number control composition are used to make standard curves for HPV type target polynucleotides and human beta-globin polynucleotide.

32. The method of claim 1, wherein copy numbers of at least two target polynucleotides are assessed.

* * * * *